(12) United States Patent
Hopper

(10) Patent No.: US 9,932,629 B2
(45) Date of Patent: Apr. 3, 2018

(54) NUCLEIC ACID AMPLIFICATION AND DETECTION KIT

(71) Applicant: Axxin Pty Ltd, Richmond (AU)

(72) Inventor: William R. Hopper, East Ivanhoe (AU)

(73) Assignee: Axxin Pty Ltd, Richmond (AU)

( * ) Notice: Subject to any disclaimer, the term of this patent is extended or adjusted under 35 U.S.C. 154(b) by 424 days.

(21) Appl. No.: 14/411,203

(22) PCT Filed: Jun. 26, 2013

(86) PCT No.: PCT/AU2013/000693
§ 371 (c)(1),
(2) Date: Dec. 24, 2014

(87) PCT Pub. No.: WO2014/000037
PCT Pub. Date: Jan. 3, 2014

(65) Prior Publication Data
US 2015/0203904 A1    Jul. 23, 2015

Related U.S. Application Data

(60) Provisional application No. 61/664,654, filed on Jun. 26, 2012.

(51) Int. Cl.
*C12Q 1/68* (2006.01)
*B01L 3/00* (2006.01)

(52) U.S. Cl.
CPC ............ *C12Q 1/6844* (2013.01); *B01L 3/502* (2013.01); *B01L 3/5023* (2013.01);
(Continued)

(58) Field of Classification Search
None
See application file for complete search history.

(56) References Cited

U.S. PATENT DOCUMENTS

| 4,234,540 A | 11/1980 | Ginsberg et al. |
| 4,250,266 A | 2/1981 | Wade |

(Continued)

FOREIGN PATENT DOCUMENTS

| EP | 1059523 B1 | 7/2007 |
| EP | 2123360 A1 | 11/2009 |

(Continued)

OTHER PUBLICATIONS

Pipper et al.; Clockwork PCR including sample preparation; Angew. Chem. Int. Ed.; 47(21); pp. 3900-3904; Apr. 15, 2008.

(Continued)

*Primary Examiner* — Samuel C Woolwine
(74) *Attorney, Agent, or Firm* — Shay Glenn LLP

(57) ABSTRACT

A nucleic acid amplification and detection kit, including: a buffer storage assembly, including a buffer storage reservoir storing a buffer solution therein; a nucleic acid amplification assembly including a nucleic acid amplification reservoir storing one or more reagents therein and configured to receive a sample containing nucleic acid for amplification therein, wherein the buffer storage assembly is configured to couple with the nucleic acid amplification assembly to seal within the nucleic acid amplification reservoir the sample containing nucleic acid and amplification products of the amplification; and a test strip assembly including a lateral flow test strip disposed therein, the test strip assembly and the coupled nucleic acid amplification and buffer storage assemblies being configured to couple with one another and including one or more solution release components to release the amplification products from the nucleic acid amplification reservoir onto the lateral flow test strip for testing, and to release the stored buffer solution from the buffer storage reservoir to flush the released amplification products along the lateral flow test strip.

22 Claims, 20 Drawing Sheets

(52) U.S. Cl.
CPC ..... *B01L 3/50825* (2013.01); *B01L 2200/026* (2013.01); *B01L 2200/027* (2013.01); *B01L 2300/047* (2013.01); *B01L 2300/049* (2013.01); *B01L 2300/0663* (2013.01); *B01L 2300/0672* (2013.01); *B01L 2300/0867* (2013.01); *B01L 2400/0406* (2013.01); *B01L 2400/0475* (2013.01); *C12Q 1/686* (2013.01); *C12Q 1/6848* (2013.01)

(56) References Cited

U.S. PATENT DOCUMENTS

| | | | |
|---|---|---|---|
| 5,152,965 | A | 10/1992 | Fisk et al. |
| 5,955,351 | A | 9/1999 | Gerdes et al. |
| 2002/0031768 | A1 | 3/2002 | McMillan et al. |
| 2003/0170686 | A1 | 9/2003 | Hoet et al. |
| 2004/0265173 | A1 | 12/2004 | Matsumoto et al. |
| 2005/0142031 | A1 | 6/2005 | Wickstead et al. |
| 2006/0223172 | A1 | 10/2006 | Bedingham et al. |
| 2006/0270027 | A1 | 11/2006 | Shaw et al. |
| 2006/0275922 | A1 | 12/2006 | Gould et al. |
| 2006/0292035 | A1 | 12/2006 | Gould et al. |
| 2008/0020380 | A1 | 1/2008 | Patno et al. |
| 2008/0287308 | A1 | 11/2008 | Hubbell et al. |
| 2009/0181388 | A1 | 7/2009 | You et al. |
| 2009/0204997 | A1 | 8/2009 | Xu et al. |
| 2011/0039261 | A1* | 2/2011 | Hillebrand ............ B01L 3/5023 435/6.14 |
| 2014/0377766 | A1 | 12/2014 | Hopper |

FOREIGN PATENT DOCUMENTS

| | | |
|---|---|---|
| EP | 2163999 A2 | 3/2010 |
| WO | WO92/08986 A1 | 5/1992 |
| WO | WO99/57561 A2 | 11/1999 |
| WO | WO2006/047777 A2 | 5/2006 |
| WO | WO2007/005077 A1 | 1/2007 |
| WO | WO2008/005248 A2 | 1/2008 |
| WO | WO 2009/132268 A1 | 10/2009 |
| WO | WO2010/030686 A1 | 3/2010 |
| WO | WO2010/104478 A1 | 9/2010 |
| WO | WO2013/113054 A1 | 8/2013 |

OTHER PUBLICATIONS

Gubala et al.; Point of care diagnostics: status and future; Analytical Chemistry; 84(2); pp. 487-515; Jan. 2012.

Cikos et al.; Transformation of real-time PCR fluorescence data to target gene quantity; Analytiical Biochemistry; 384(1); pp. 1-10; Jan. 1, 2009.

Durtschi et al.; Evaluation of quantification methods for real-time PCR minor groove binding hybridization probe assays; Analytical Biochemistry; 361(1); pp. 55-64; Jan. 4, 2007.

Liu et al.; Progress curve analysis of qRT-PCR reactions using the logistic growth equation; Biotechnology Progress; 27(5); pp. 1407-1414; Sep. 15, 2011.

Roche Diagnostics GMBH; LightCycler 480 Instrument Operator's Manual, Software version 1.5; ©2008; 8 pages; Oct. 15, 2014; retrieved from the internet (http://pedrovale.files.wordpress.com/2013/08/lightcyclerc2ae-480-instrument-operators-manual.pdf).

Wikipedia; Immunoassay; 4 pages; Feb. 24, 2015; retrieved from the internet (http://en.wikiopedia.org/wiki/Immunoassay).

Wikipedia; Lateral flow test; 4 pages; Feb. 24, 2015; retrieved from the Internet (http:en.wikipedia.org/wiki/Lateral_flow_test).

Wikipedia; Polymerase chain reaction; 13 pages; Oct. 15, 2014; retrieved from the internet (http://en.wikipedia.org/wiki/Polymerase_chain_reaction).

Wikipedia; Variants of PCR; 11 pages; Oct. 15, 2014; retrieved from the internet (http://en.wikipedia.org/wiki/Variants_of_PCR#Isothermal_amplification_methods).

\* cited by examiner

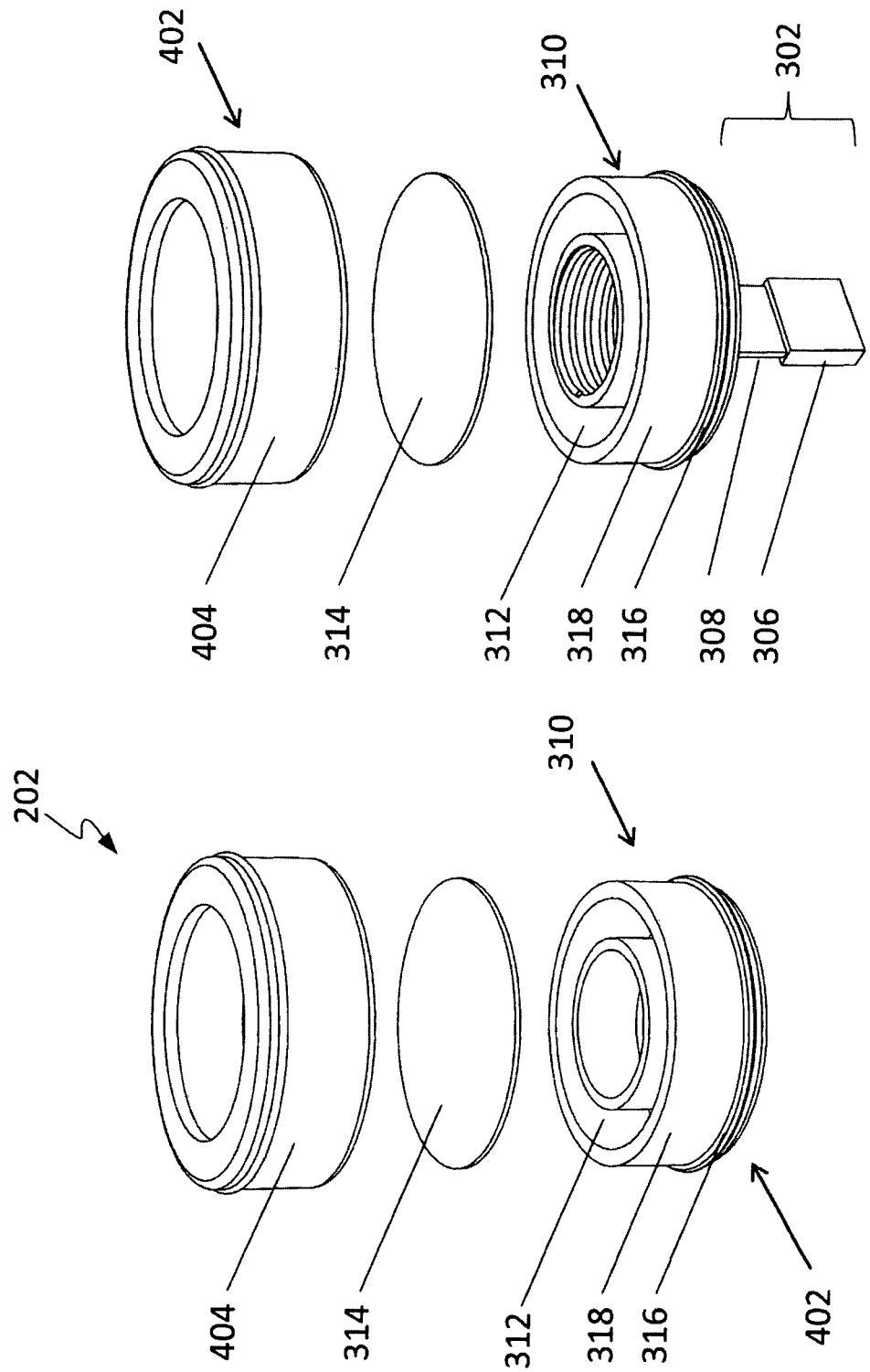

NUCLEIC ACID AMPLIFICATION AND DETECTION KIT

TECHNICAL FIELD

The present invention relates to a nucleic acid amplification and detection kit or apparatus.

BACKGROUND

As described in the Wikipedia at en.wikipedia.org/wiki/Immunoassay: the Wikipedia text quoted herein is released under CC-BY-SA, see creativecommons.orelicenses/by-sa/3.0.

"An immunoassay test is a biochemical test that measures the concentration of a substance in a biological liquid, typically serum or urine, using the reaction of an antibody or antibodies to its antigen. The assay takes advantage of the specific binding of an antibody to its antigen. Monoclonal antibodies are often used as they only usually bind to one site of a particular molecule, and therefore provide a more specific and accurate test, which is less easily confused by the presence of other molecules. The antibodies picked must have a high affinity for the antigen (if there is antigen available, a very high proportion of it must bind to the antibody).

Both the presence of antigen or antibodies can be measured. For instance, when seeking to detect the presence of an infection the concentration of antibody specific to that particular pathogen is measured. For measuring hormones such as insulin, the insulin acts as the antigen.

For numerical results, the response of the fluid being measured must be compared to standards of a known concentration. This is usually done though the plotting of a standard curve on a graph, the position of the curve at response of the unknown is then examined, and so the quantity of the unknown found.

Detecting the quantity of antibody or antigen can be achieved by a variety of methods. One of the most common is to label either the antigen or antibody. The label may consist of an enzyme, enzyme immunoassay (EIA)), radioisotopes such as I-125 Radioimmunoassay (RIA), magnetic labels (magnetic immunoassay— MIA) or fluorescence. Other techniques include agglutination, nephelometry, turbidimetry and Western Blot. A number of these do form a directly visible line or test output but require an instrument to measure or capture the test output.

Immunoassays can be divided into those that involve labelled reagents and those which involve non-labelled reagents. Those which involve labelled reagents are divided into homogenous and heterogeneous (which require an extra step to remove unbound antibody or antigen from the site, usually using a solid phase reagent) immunoassays. Heterogeneous immunoassays can be competitive or non-competitive.

In a competitive immunoassay, the antigen in the unknown sample competes with labelled antigen to bind with antibodies. The amount of labelled antigen bound to the antibody site is then measured. In this method, the response will be inversely proportional to the concentration of antigen in the unknown. This is because the greater the response, the less antigen in the unknown was available to compete with the labelled antigen.

In non-competitive immunoassays, also referred to as the "sandwich assay," antigen in the unknown is bound to the antibody site, and then labelled antibody is bound to the antigen. The amount of labelled antibody on the site is then measured. Unlike the competitive method, the results of the non-competitive method will be directly proportional to the concentration of the antigen. This is because labelled antibody will not bind if the antigen is not present in the unknown sample.

Because homogeneous assays do not require this step, they are typically faster and easier to perform."

As described in the Wikipedia at en.wikipedia.org/wiki/Lateral flow test:

"Lateral flow tests also known as Lateral Flow Immunochromatographic Assays are a simple device intended to detect the presence (or absence) of a target analyte in sample (matrix). Most commonly these tests are used for medical diagnostics either for home testing, point of care testing, or laboratory use. Often produced in a dipstick format, Lateral flow tests are a form of immunoassay in which the test sample flows along a solid substrate via capillary action. After the sample is applied to the test it encounters a coloured reagent which mixes with the sample and transits the substrate encountering lines or zones which have been pre-treated with an antibody or antigen. Depending upon the analytes present in the sample the coloured reagent can become bound at the test line or zone. Lateral Flow Tests can operate as either competitive or sandwich assays.

In principle any coloured particle can be used, however most tests commonly use either latex (blue colour) or nanometer sized particles of gold (red colour). The gold particles are red in colour due to localized surface Plasmon resonance. Fluorescent or magnetic labelled particles can also be used—however these require the use of an electronic reader to access the test result.

The sample first encounters coloured particles which are labelled with antibodies raised to the target analyte. The test line will also contain antibodies to the same target, although it may bind to a different epitope on the analyte.

The test line will show as a coloured band in positive samples.

The sample first encounters coloured particles which are labelled with the target analyte or an analogue. The test line contains antibodies to the target/its analogue. Unlabelled analyte in the sample will block the binding sites on the antibodies preventing uptake of the coloured particles.

The test line will show as a coloured band in negative samples.

Most tests are intended to operate on a purely qualitative basis. However it is possible to measure the intensity of the test line to determine the quantity of analyte in the sample. Implementing a Magnetic immunoassay (MIA) in the lateral flow test form also allows for getting a quantified result.

While not strictly necessary, most tests will incorporate a second line which contains an antibody that picks up free latex/gold in order to confirm the test has operated correctly.

Time to obtain the test result is a key driver for these products. Tests can take as little as a few minutes to develop. Generally there is a trade-off between time and sensitivity—so more sensitive tests may take longer to develop. The other key advantage of this format of test compared to other immunoassays is the simplicity of the test—typically requiring little or no sample or reagent preparation.

Probably the most well known examples of lateral flow tests are home pregnancy tests. However rapid tests or point of care tests are available for a wide range of applications including: HIV tests, Troponin T, test Malaria tests, drugs of Abuse tests, Fertility tests, Respiratory disease tests etc. Clinical tests can be applied to urine, saliva, blood, or stool samples. Tests are available for both human and animal diagnostics. Tests are also available for non clinical applications including testing food and water for contaminants."

FIG. 1 shows a typical lateral flow strip as commonly used in rapid diagnostic applications. The strip contains a sample application pad 102, a conjugate pad 104, a membrane (typically nitrocellulose) 106 along which an analyte flows, and a waste absorbing pad 108. These components are bonded by an adhesive layer 110 onto a carrier strip 112, usually constructed from plastic sheet.

Immobilised on the membrane 106 are one or more test line(s) 114 containing capture antigens or antibodies for the target(s) of interest, and a control line 116 containing a control capture antigen or antibody. The test line(s) 114 also include visible or coloured or fluorescent labels so that the test result is displayed in the form of visible or otherwise optically detectable lines of the test and control lines 114, 116.

The lateral flow strip described above and shown in FIG. 1 may also be contained in a plastic cassette having an opening for sample introduction and an open "window" for viewing the test and control lines 114, 116.

Currently, such lateral flow strips and other similar types of biomedical test strips are widely used to diagnose a wide variety of medical conditions, including pregnancy, health markers, and infectious diseases, including flu, for example.

Nucleic Acid Amplification

The amplification of nucleic acids is important in many fields, including medical, biomedical, environmental, veterinary and food safety testing. In general, nucleic acids are amplified by one of two methods: polymerase chain reaction (PCR) or isothermal amplification, both of which are described below.

Polymerase Chain Reaction (PCR)

As described in the Wikipedia at en.wikipedia.org/wiki/Polymerase chain reaction: the Wikipedia text quoted herein is released under CC-BY-SA, see creativecommons.org/licenses/by-sa/3.0.

"The polymerase chain reaction (PCR) is a scientific technique in molecular biology to amplify a single or a few copies of a piece of DNA across several orders of magnitude, generating thousands to millions of copies of a particular DNA sequence.

Developed in 1983 by Kary Mullis, PCR is now a common and often indispensable technique used in medical and biological research labs for a variety of applications. These include DNA cloning for sequencing, DNA-based phylogeny, or functional analysis of genes; the diagnosis of hereditary diseases; the identification of genetic fingerprints (used in forensic sciences and paternity testing); and the detection and diagnosis of infectious diseases. In 1993, Mullis was awarded the Nobel Prize in Chemistry along with Michael Smith for his work on PCR.

The method relies on thermal cycling, consisting of cycles of repeated heating and cooling of the reaction for DNA melting and enzymatic replication of the DNA. Primers (short DNA fragments) containing sequences complementary to the target region along with a DNA polymerase (after which the method is named) are key components to enable selective and repeated amplification. As PCR progresses, the DNA generated is itself used as a template for replication, setting in motion a chain reaction in which the DNA template is exponentially amplified. PCR can be extensively modified to perform a wide array of genetic manipulations.

Almost all PCR applications employ a heat-stable DNA polymerase, such as Taq polymerase, an enzyme originally isolated from the bacterium *Thermus aquaticus*. This DNA polymerase enzymatically assembles a new DNA strand from DNA building-blocks, the nucleotides, by using single-stranded DNA as a template and DNA oligonucleotides (also called DNA primers), which are required for initiation of DNA synthesis. The vast majority of PCR methods use thermal cycling, i.e., alternately heating and cooling the PCR sample to a defined series of temperature steps. These thermal cycling steps are necessary first to physically separate the two strands in a DNA double helix at a high temperature in a process called DNA melting. At a lower temperature, each strand is then used as the template in DNA synthesis by the DNA polymerase to selectively amplify the target DNA. The selectivity of PCR results from the use of primers that are complementary to the DNA region targeted for amplification under specific thermal cycling conditions.

PCR Principles and Procedure

PCR is used to amplify a specific region of a DNA strand (the DNA target). Most PCR methods typically amplify DNA fragments of up to ~10 kilo base pairs (kb), although some techniques allow for amplification of fragments up to 40 kb in size.

A basic PCR set up requires several components and reagents. These components include:

DNA template that contains the DNA region (target) to be amplified.

Two primers that are complementary to the 3' (three prime) ends of each of the sense and anti-sense strand of the DNA target.

Taq polymerase or another DNA polymerase with a temperature optimum at around 70° C.

Deoxynucleoside triphosphates (dNTPs; nucleotides containing triphosphate groups), the building-blocks from which the DNA polymerase synthesizes a new DNA strand.

Buffer solution, providing a suitable chemical environment for optimum activity and stability of the DNA polymerase.

Divalent cations, magnesium or manganese ions; generally $Mg^{2+}$ is used, but $Mn^{2+}$ can be utilized for PCR-mediated DNA mutagenesis, as higher $Mn^{2+}$ concentration increases the error rate during DNA synthesis.

Monovalent cation potassium ions.

The PCR is commonly carried out in a reaction volume of 10-200 μl in small reaction tubes (0.2-0.5 ml volumes) in a thermal cycler. The thermal cycler heats and cools the reaction tubes to achieve the temperatures required at each step of the reaction (see below). Many modern thermal cyclers make use of the Peltier effect, which permits both heating and cooling of the block holding the PCR tubes simply by reversing the electric current. Thin-walled reaction tubes permit favorable thermal conductivity to allow for rapid thermal equilibration. Most thermal cyclers have heated lids to prevent condensation at the top of the reaction tube. Older thermocyclers lacking a heated lid require a layer of oil on top of the reaction mixture or a ball of wax inside the tube.

Procedure

Typically, PCR consists of a series of 20-40 repeated temperature changes, called cycles, with each cycle commonly consisting of 2-3 discrete temperature steps, usually three. The cycling is often preceded by a single temperature step (called hold) at a high temperature (>90° C.), and followed by one hold at the end for final product extension or brief storage. The temperatures used and the length of time they are applied in each cycle depend on a variety of parameters. These include the enzyme used for DNA synthesis, the concentration of divalent ions and dNTPs in the reaction, and the melting temperature (Tm) of the primers.

Initialization step: This step consists of heating the reaction to a temperature of 94-96° C. (or 98° C. if extremely thermostable polymerases are used), which is held for 1-9 minutes. It is only required for DNA polymerases that require heat activation by hot-start PCR.

Denaturation step: This step is the first regular cycling event and consists of heating the reaction to 94-98° C. for 20-30 seconds. It causes DNA melting of the DNA template by disrupting the hydrogen bonds between complementary bases, yielding single-stranded DNA molecules.

Annealing step: The reaction temperature is lowered to 50-65° C. for 20-40 seconds allowing annealing of the primers to the single-stranded DNA template. Typically the annealing temperature is about 3-5 degrees Celsius below the Tm of the primers used. Stable DNA-DNA hydrogen bonds are only formed when the primer sequence very closely matches the template sequence. The polymerase binds to the primer-template hybrid and begins DNA synthesis.

Extension/elongation step: The temperature at this step depends on the DNA polymerase used; Taq polymerase has its optimum activity temperature at 75-80° C., and commonly a temperature of 72° C. is used with this enzyme. At this step the DNA polymerase synthesizes a new DNA strand complementary to the DNA template strand by adding dNTPs that are complementary to the template in 5' to 3' direction, condensing the 5'-phosphate group of the dNTPs with the 3'-hydroxyl group at the end of the nascent (extending) DNA strand. The extension time depends both on the DNA polymerase used and on the length of the DNA fragment to be amplified. As a rule-of-thumb, at its optimum temperature, the DNA polymerase will polymerize a thousand bases per minute. Under optimum conditions, i.e., if there are no limitations due to limiting substrates or reagents, at each extension step, the amount of DNA target is doubled, leading to exponential (geometric) amplification of the specific DNA fragment.

Final elongation: This single step is occasionally performed at a temperature of 70-74° C. for 5-15 minutes after the last PCR cycle to ensure that any remaining single-stranded DNA is fully extended.

Final hold: This step at 4-15° C. for an indefinite time may be employed for short-term storage of the reaction.

To check whether the PCR generated the anticipated DNA fragment (also sometimes referred to as the amplimer or amplicon), agarose gel electrophoresis is employed for size separation of the PCR products. The size(s) of PCR products is determined by comparison with a DNA ladder (a molecular weight marker), which contains DNA fragments of known size, run on the gel alongside the PCR products.

PCR Stages

The PCR process can be divided into three stages:

Exponential amplification: At every cycle, the amount of product is doubled (assuming 100% reaction efficiency). The reaction is very sensitive: only minute quantities of DNA need to be present.

Leveling off stage: The reaction slows as the DNA polymerase loses activity and as consumption of reagents such as dNTPs and primers causes them to become limiting.

Plateau: No more product accumulates due to exhaustion of reagents and enzyme.

PCR Optimization

In practice, PCR can fail for various reasons, in part due to its sensitivity to contamination causing amplification of spurious DNA products. Because of this, a number of techniques and procedures have been developed for optimizing PCR conditions. Contamination with extraneous DNA is addressed with lab protocols and procedures that separate pre-PCR mixtures from potential DNA contaminants. This usually involves spatial separation of PCR-setup areas from areas for analysis or purification of PCR products, use of disposable plasticware, and thoroughly cleaning the work surface between reaction setups. Primer-design techniques are important in improving PCR product yield and in avoiding the formation of spurious products, and the usage of alternate buffer components or polymerase enzymes can help with amplification of long or otherwise problematic regions of DNA. Addition of reagents, such as formamide, in buffer systems may increase the specificity and yield of PCR.

Amplification and Quantification of DNA

Because PCR amplifies the regions of DNA that it targets, PCR can be used to analyze extremely small amounts of sample. This is often critical for forensic analysis, when only a trace amount of DNA is available as evidence. PCR may also be used in the analysis of ancient DNA that is tens of thousands of years old. These PCR-based techniques have been successfully used on animals, such as a forty-thousand-year-old mammoth, and also on human DNA, in applications ranging from the analysis of Egyptian mummies to the identification of a Russian tsar.

Quantitative PCR methods allow the estimation of the amount of a given sequence present in a sample—a technique often applied to quantitatively determine levels of gene expression. Real-time PCR is an established tool for DNA quantification that measures the accumulation of DNA product after each round of PCR amplification.

PCR in Diagnosis of Diseases

PCR permits early diagnosis of malignant diseases such as leukemia and lymphomas, which is currently the highest-developed in cancer research and is already being used routinely. (See the studies cited in the EUTOS For CML study article at eutos.org/content/molecular_monitoring/information/pcr_testing/, especially notes 10-13.) PCR assays can be performed directly on genomic DNA samples to detect translocation-specific malignant cells at a sensitivity that is at least 10,000-fold higher than that of other methods.

PCR also permits identification of non-cultivatable or slow-growing microorganisms such as mycobacteria, anaerobic bacteria, or viruses from tissue culture assays and animal models. The basis for PCR diagnostic applications in microbiology is the detection of infectious agents and the discrimination of non-pathogenic from pathogenic strains by virtue of specific genes.

Viral DNA can likewise be detected by PCR. The primers used need to be specific to the targeted sequences in the DNA of a virus, and the PCR can be used for diagnostic analyses or DNA sequencing of the viral genome. The high sensitivity of PCR permits virus detection soon after infection and even before the onset of disease. Such early detection may give physicians a significant lead in treatment. The amount of virus ("viral load") in a patient can also be quantified by PCR-based DNA quantitation techniques (see below).

Isothermal Amplification Methods

As described in the Wikipedia at en.wikipedia.org/wiki/Variants_of_PCR#Isothermal_amplification_met-hods:

"Some DNA amplification protocols have been developed that may be used alternatively to PCR:

Helicase-dependent amplification is similar to traditional PCR, but uses a constant temperature rather than cycling through denaturation and annealing/extension steps. DNA Helicase, an enzyme that unwinds DNA, is used in place of thermal denaturation.

PAN-AC also uses isothermal conditions for amplification, and may be used to analyze living cells.

1. Nicking Enzyme Amplification Reaction referred to as NEAR, is isothermal, replicating DNA at a constant temperature using a polymerase and nicking enzyme.

Recombinase Polymerase Amplification (RPA). The method uses a recombinase to specifically pair primers with double-stranded DNA on the basis of homology, thus directing DNA synthesis from defined DNA sequences present in the sample. Presence of the target sequence initiates DNA amplification, and no thermal or chemical melting of DNA is required. The reaction progresses rapidly and results in specific DNA amplification from just a few target copies to detectable levels typically within 5-10 minutes. The entire reaction system is stable as a dried formulation and does not need refrigeration. RPA can be used to replace PCR (Polymerase Chain Reaction) in a variety of laboratory applications and users can design their own assays.

Detection of the Amplification Products

Existing immunoassay tests such as lateral flow tests are often limited by sensitivity, particularly where only small amounts of the target material or antigen such as viral DNA being tested for are present in the sample. DNA amplification has the advantage that it can significantly improve the sensitivity of a test which involves detection of DNA as it provides a huge increase in the presence of the target DNA in the sample under test. However, diagnostic tests based on DNA amplification typically require a complex instrument to perform accurate thermocycling in reasonable times and to instrument the detection stage which may use expensive detection technologies such as fluorescence detection or sensitive bioluminescence detection with devices such as photomultiplier tubes and complex optics. Even where a simple isothermal DNA amplification approach is used, the same complex instrumental detection is typically required.

Performing DNA amplification prior to detection using lateral flow has the advantage that it allows for a simpler test format with a potentially non-instrumented detection using visual inspection of test lines on the lateral flow strip. Even where instrumented detection of the lateral flow strip is desirable for reasons of repeatability, consistency and sensitivity, the instrumentation and sensor required to read a lateral flow strip can be significantly less costly, more compact, and less complex than those required to read chemical or fluorescent beacons or probes directly in the fluid products from DNA amplification.

Using a lateral flow strip test as the detection and display following DNA amplification is an established technique. However, the inventor has identified a number of difficulties or shortcomings of such prior art methods and apparatus. Firstly, they will typically involve a number of manual steps that make the approach susceptible to error, and add time and complexity for the user. In particular, the manual steps required to separate a sample, add it to a DNA amplification mix, provide amplification, decant the amplified product onto a test strip and then flush the strip with a buffer solution—are unsuitable for many applications, including:

(i) simple point of care or field-deployed diagnostic;
(ii) operation by untrained or non-technical users; and
(iii) tests suitable for CLIA waver approval for a diagnostic test in the USA.

A further difficulty with a manually operated, exposed or partially exposed test process of this diagnostic approach is the risk of release of amplified products into the test environment. The amplified solution can contain millions or billions of amplified DNA material, and/or segments of the target DNA under test. If these are transferred from an amplification chamber to a lateral flow test strip in a way that can leak or contaminate the user or the surrounding work area, then any following tests will be contaminated. Any of the released amplification products that contaminate samples for subsequent tests will themselves be amplified and thereby result in false positive results. Moreover, a work area or room contaminated by amplification products may be very difficult to decontaminate, and will introduce false positive results and uncertainty compromising all further use of the diagnostic test.

It is desired, therefore, to provide a nucleic acid amplification and detection kit, apparatus, and/or method that alleviates one or more difficulties of the prior art, or that at least provides a useful alternative.

SUMMARY

In accordance with some embodiments of the present invention, there is provided a nucleic acid amplification and detection kit, including:

a buffer storage assembly, including a buffer storage reservoir storing a buffer solution therein;

a nucleic acid amplification assembly including a nucleic acid amplification reservoir storing one or more reagents therein and configured to receive a sample containing nucleic acid for amplification therein, wherein the buffer storage assembly is configured to couple with the nucleic acid amplification assembly to seal within the nucleic acid amplification reservoir the sample containing nucleic acid and amplification products of said amplification; and a test strip assembly including a lateral flow test strip disposed therein, the test strip assembly and the coupled nucleic acid amplification and buffer storage assemblies being configured to couple with one another and including one or more solution release components to release the amplification products from the nucleic acid amplification reservoir onto the lateral flow test strip for testing, and to release the stored buffer solution from the buffer storage reservoir to flush the released amplification products along the lateral flow test strip.

In some embodiments, the solution release components are configured to release the amplification products onto the lateral flow test strip prior to releasing the buffer solution onto the lateral flow test strip.

In some embodiments, the buffer storage reservoir includes a rupturable membrane that seals the buffer solution within the buffer storage reservoir, and the solution release components includes at least one buffer release component that ruptures the membrane to allow said release of the buffer solution from the buffer storage reservoir.

In some embodiments, a first portion of the rupturable membrane seals the buffer solution within the buffer storage reservoir, and a second portion of the rupturable membrane seals the amplification products within the nucleic acid amplification reservoir, and the solution release means includes at least one amplification products release component that ruptures the second portion of the membrane to allow release of the amplification products from the nucleic acid amplification reservoir.

In some embodiments, the amplification products release component includes a projection that projects into the nucleic acid amplification reservoir to displace the amplification products therefrom.

In some embodiments, the solution release components are configured to automatically release the amplification products and the stored buffer solution during coupling of the test strip assembly to the coupled nucleic acid amplification and buffer storage assemblies.

In some embodiments, the test strip assembly is coupled to the coupled nucleic acid amplification and buffer storage assemblies by a screwing action.

In some embodiments, the nucleic acid amplification and detection kit includes a test strip assembly locking component to prevent or at least inhibit decoupling of the test strip assembly from the coupled nucleic acid amplification and buffer storage assemblies.

In some embodiments, the nucleic acid amplification and detection kit includes a nucleic acid amplification assembly locking component to prevent or at least inhibit decoupling of the coupled nucleic acid amplification and buffer storage assemblies.

In some embodiments, the buffer storage assembly includes a cap or lid incorporating the buffer storage reservoir, and the buffer storage reservoir is in the form of an annular cavity within the cap or lid, the cavity being sealed by a rupturable membrane disposed on the outer surface of the cap or lid when the cap or lid seals the nucleic acid amplification reservoir.

In some embodiments, the nucleic acid amplification assembly includes a generally cylindrical support to support the nucleic acid amplification reservoir, the support being configured to couple with the buffer storage assembly and with the test strip assembly, the nucleic acid amplification reservoir being in the form of a PCR tube having a removable sealing component.

In some embodiments, the removable sealing component is in the form of a plug having a handle to facilitate removal of the plug from the nucleic acid amplification reservoir by a user.

In some embodiments, the support is configured to couple with the buffer storage assembly in an upright orientation so that the amplification products are retained at the base of the PCR tube by gravity, and to couple with the test strip assembly in an inverted orientation so that gravity acts to draw the amplification products away from the base of the PCR tube.

In some embodiments, the nucleic acid amplification reservoir stores one or more magnetic beads in addition to the one or more reagents.

In some embodiments, the nucleic acid amplification and detection kit includes one or more decontamination components configured to automatically destroy the amplification products subsequent to said testing.

In some embodiments, the decontamination components include a slow acting decontamination agent included in the buffer solution.

In some embodiments, the decontamination components include a decontamination agent stored in a waste pad of the lateral flow test strip, whereby backflow from the waste pad decontaminates the lateral flow test strip.

In some embodiments, the buffer storage assembly includes a sample capture component for capturing a sample containing nucleic acid, the sample capture component being arranged so that the act of coupling the buffer storage assembly to the nucleic acid amplification assembly requires the sample capture component to be introduced into the nucleic acid amplification reservoir, thereby also introducing the captured sample containing nucleic acid into the nucleic acid amplification reservoir for amplification therein.

In some embodiments, the buffer storage assembly includes a cap or lid incorporating the buffer storage reservoir, and the sample capture component includes an absorbent pad disposed at one end of an elongate member, the other end of the elongate member being attached to the cap or lid.

In some embodiments, the buffer storage assembly is configured to couple with the nucleic acid amplification assembly by introducing the absorbent pad and elongate member into the nucleic acid amplification reservoir and then sealing the nucleic acid amplification reservoir with the cap or lid.

In accordance with some embodiments of the present invention, there is provided a nucleic acid amplification and detection method, including:
  introducing a sample containing nucleic acid into a nucleic acid amplification reservoir of a nucleic acid amplification assembly;
  coupling to the nucleic acid amplification assembly a buffer storage assembly to seal the sample containing nucleic acid within the nucleic acid amplification reservoir, the buffer storage assembly including a buffer storage reservoir storing a buffer solution therein;
  performing nucleic acid amplification to generate amplification products within the sealed nucleic acid amplification reservoir;
  inverting the coupled buffer storage and nucleic acid amplification assemblies to facilitate removal of the amplification products therefrom;
  coupling the coupled buffer storage and nucleic acid amplification assemblies to a test strip assembly including a lateral flow test strip disposed therein;
  releasing the amplification products from the nucleic acid amplification reservoir onto the lateral flow test strip; and releasing the buffer solution from the nucleic acid amplification reservoir onto the lateral flow test strip to flush the amplification products along the lateral flow test strip;

wherein the amplification products remain sealed within the coupled assemblies.

Also described herein is a nucleic acid amplification and detection apparatus, including:
 a buffer storage assembly, including a buffer storage reservoir storing a buffer solution therein;
 a nucleic acid amplification assembly including a nucleic acid amplification reservoir storing one or more reagents therein and configured to receive a sample containing nucleic acid for amplification therein, wherein the buffer storage assembly is configured to couple with the nucleic acid amplification assembly to seal within the nucleic acid amplification reservoir the sample containing nucleic acid and amplification products of said amplification; and
 a test strip assembly including a lateral flow test strip disposed therein, the test strip assembly and the coupled nucleic acid amplification and buffer storage assemblies being configured to couple with one another and including one or more solution release components to release the amplification products from the nucleic acid amplification reservoir onto the lateral flow test strip for testing, and to release the stored buffer solution from the buffer storage reservoir to flush the released amplification products along the lateral flow test strip.

In some embodiments, the method includes coupling the coupled assemblies to a test strip reader instrument to determine a test result, and exposing the coupled assemblies to a UV light source to decontaminate the coupled assemblies.

BRIEF DESCRIPTION OF THE DRAWINGS

Some embodiments of the present invention are hereinafter described, by way of example only, with reference to the accompanying drawings, wherein:

FIG. 3 is an exploded isometric view of a buffer storage assembly of the kit of FIG. 2;

FIG. 4 is an exploded isometric view of a buffer storage assembly of an alternative embodiment of the present invention;

DETAILED DESCRIPTION

Figure 1:
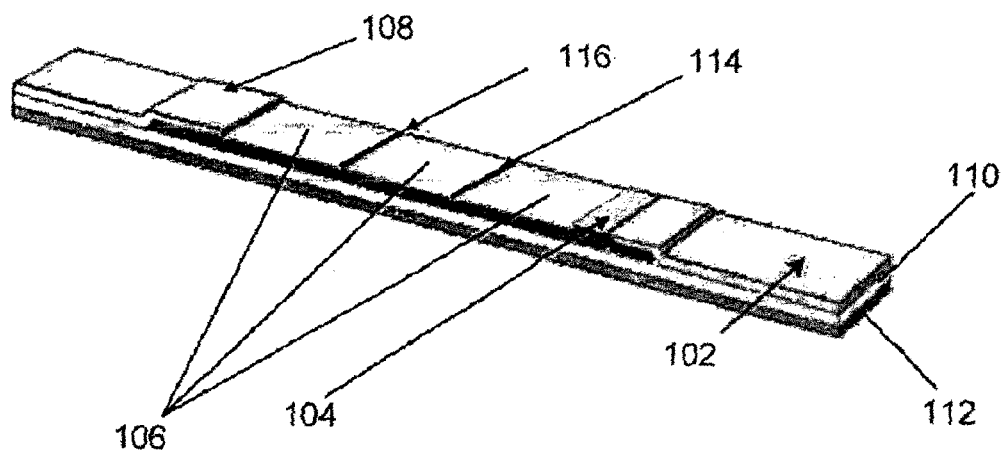
FIG. 1 is a schematic diagram of a generic prior art lateral flow strip as commonly used in rapid diagnostic applications.

Described herein is a nucleic acid amplification and detection kit or apparatus that constitutes a platform for (in some embodiments) rapidly and conveniently collecting a nucleic acid sample, performing nucleic acid amplification on the sample, and performing lateral flow tests on the resulting amplification products. Although embodiments of the present invention are described herein as a kit (or apparatus) having three major components or assemblies, in use these three components are sequentially engaged or coupled together to form a single, complete final assembly. In the described embodiment, the final assembly is most conveniently provided to end users in the form of a kit with the three constituent (and disposable) components or assemblies mutually disengaged or physically separate. However, it will be apparent that in other embodiments, some or all of these components could be provided to end users in mutually coupled form, and subsequently decoupled by the user in preparation for use.

Each of the nucleic acid amplification and detection kits described herein constitutes a convenient, low cost, and disposable apparatus or assembly that retains all of the fluid and processing within a simple workflow. In particular, the amplified product is contained and prevented from contaminating the work environment.

The workflow of a typical DNA amplification with lateral flow detection is as follows:
 (i) collect sample (for example saliva, blood, or nasal swab);
 (ii) add the collected sample to a test or buffer solution to stabilise the sample, control parameters such as its pH and viscosity, and if required provide cell wall lysis functions to expose DNA segments suitable for amplification;
 (iii) add part of the buffered treated sample solution to a DNA reaction vessel containing the amplification primers and other required amplification chemistry components (which may be in dry or liquid form);

(iv) heat at uniform temperature for iso-thermal reactions, or thermocycle for a number of cycles duration to drive DNA amplification;

(v) add some of the resulting amplified products to a lateral flow detection strip;

(vi) add a buffer solution or water to the lateral flow strip to ensure that all of the amplified products are washed through the detection regions to achieve consistent detection; and (vii) read the test lines on the lateral flow strip to determine a diagnostic test result.

All of the steps of this workflow bar the initial sample collection step can be performed using the simple disposable components of the kit described herein. Low cost, disposable parts have the significant advantage that they do not need to be cleaned and re-used. As a practical matter, the cleaning and reuse of components exposed to a test sample or derivatives thereof for a test using DNA amplification would be virtually impossible, and would cause the results of such tests to be very unreliable due to the risk of contamination.

By using very simple, low cost moulded plastic components, the kit described herein allows such tests to be cost effective and reliable, and all components can be disposed of at the end of the test in a sealed (and, in some embodiments, at least partially decontaminated) configuration containing the test sample.

Figure 2:
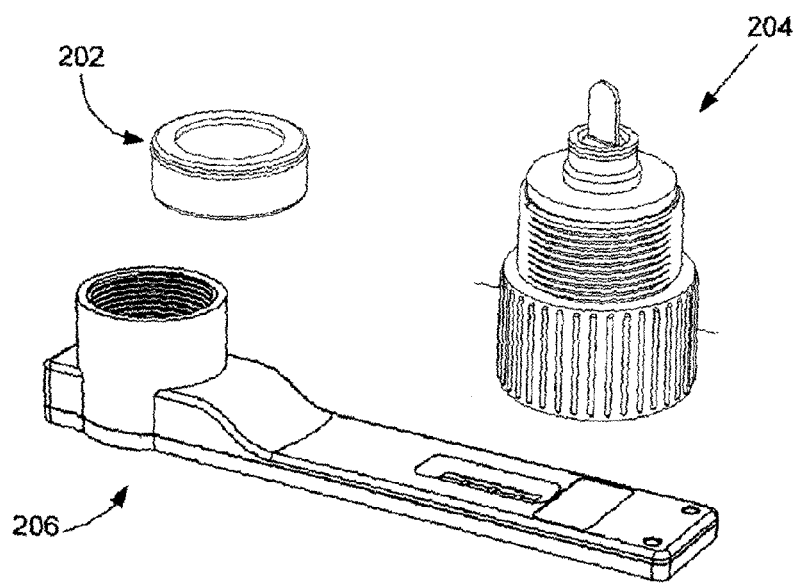
FIG. 2 is an isometric view of the three major components or assemblies of an nucleic acid amplification and detection kit or apparatus in accordance with an embodiment of the present invention.

As shown in FIG. 2, a nucleic acid amplification and detection kit includes a buffer storage assembly 202, a nucleic acid amplification assembly 204, and a lateral flow test strip assembly 206. As shown in FIG. 4, in some embodiments the buffer storage assembly 202 includes a sample collection component 302 in addition to a buffer storage and cap component 202. In other embodiments, as shown in FIG. 3, the sample collection component 302 is omitted, and sample collection can be performed independently of the kit. However, in such cases the kit can include a dropper for fluid sampling and dispensing.

As shown in FIG. 4, the sample collection component 302 includes a sample collection pad 306 disposed at one end of a pad support member or paddle 308, the other end of the paddle 308 being attached to the buffer storage and cap component 202. The buffer storage and cap component 202 includes a cap portion 310 that defines an annular internal cavity or reservoir 312 into which a buffer solution (not shown) is dispensed for storage therein. The open top of the reservoir 312 is then sealed with a frangible or rupturable circular foil seal 314 using a heat press.

As shown in FIGS. 3 and 4, a generally annular protective cap 402 having a cylindrical skirt or flange 404 is then placed over the circular foil seal 314 to protect the foil seal 314 from damage while leaving an inner circular portion of the foil seal 314 exposed to allow the stored buffer solution to be released when required, as described below.

Figure 5:
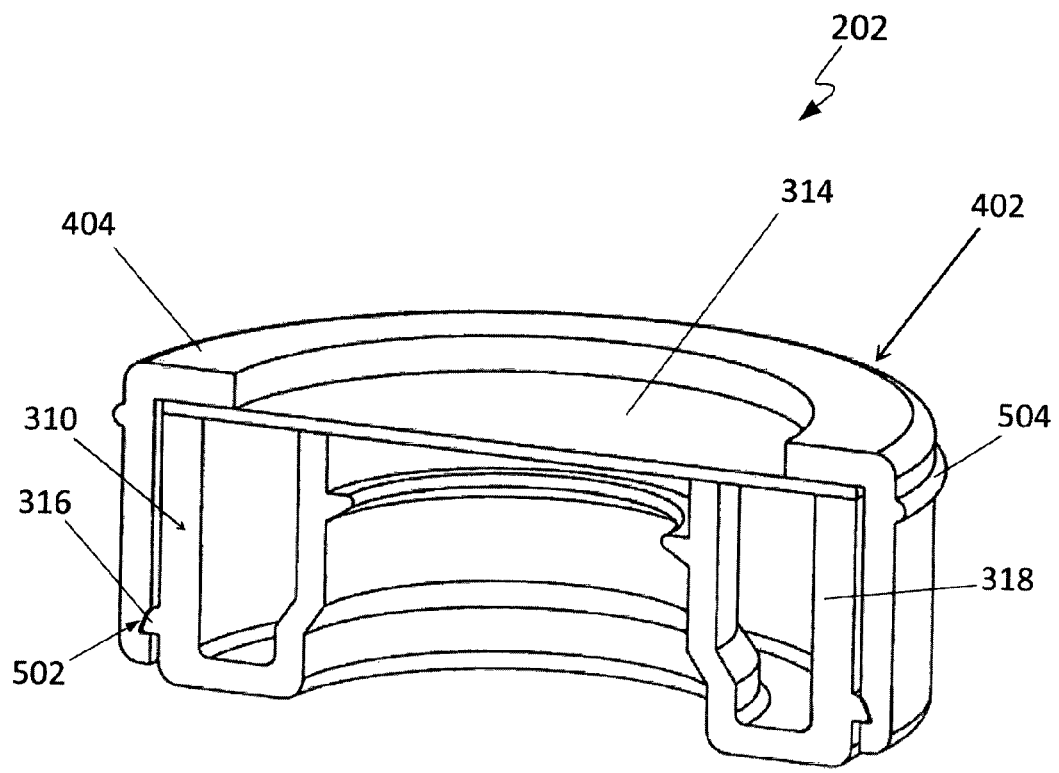
FIG. 5 is an isometric cross-sectional view of the buffer storage assembly of FIG. 3.

As shown in FIG. 5, the protective cap 402 engages with the cap portion 310 in a 'snap fit' manner by way of a circular peripheral rib 316 that projects from the outer curved surface of a cylindrical skirt 318 of the cap portion 310 and engages with a corresponding circular recess 502 on the inner cylindrical surface of the protective cap 402. Other configurations and means of engagement may be used in other embodiments. Thus as the protective cap 402 is pressed onto the cap portion 310, the projecting peripheral rib 316 causes the cylindrical skirt 318 of the cap portion 310 and the skirt of the protective cap 402 to be elastically deformed until the projecting rib 316 reaches the corresponding recess 502, at which point the complementary shapes of these features allows the stress caused by the deformation to be relieved and engages the protective cap 402 to the cap portion 310. This arrangement thus causes the protective cap 402 to lock onto the cap portion 310 in a 'snap fit' or 'click lock' manner as these components 310, 402 are pressed together. The resulting buffer storage assembly 202 is then ready for use and/or for packaging for sale or other form of distribution.

Figures 6, 7:
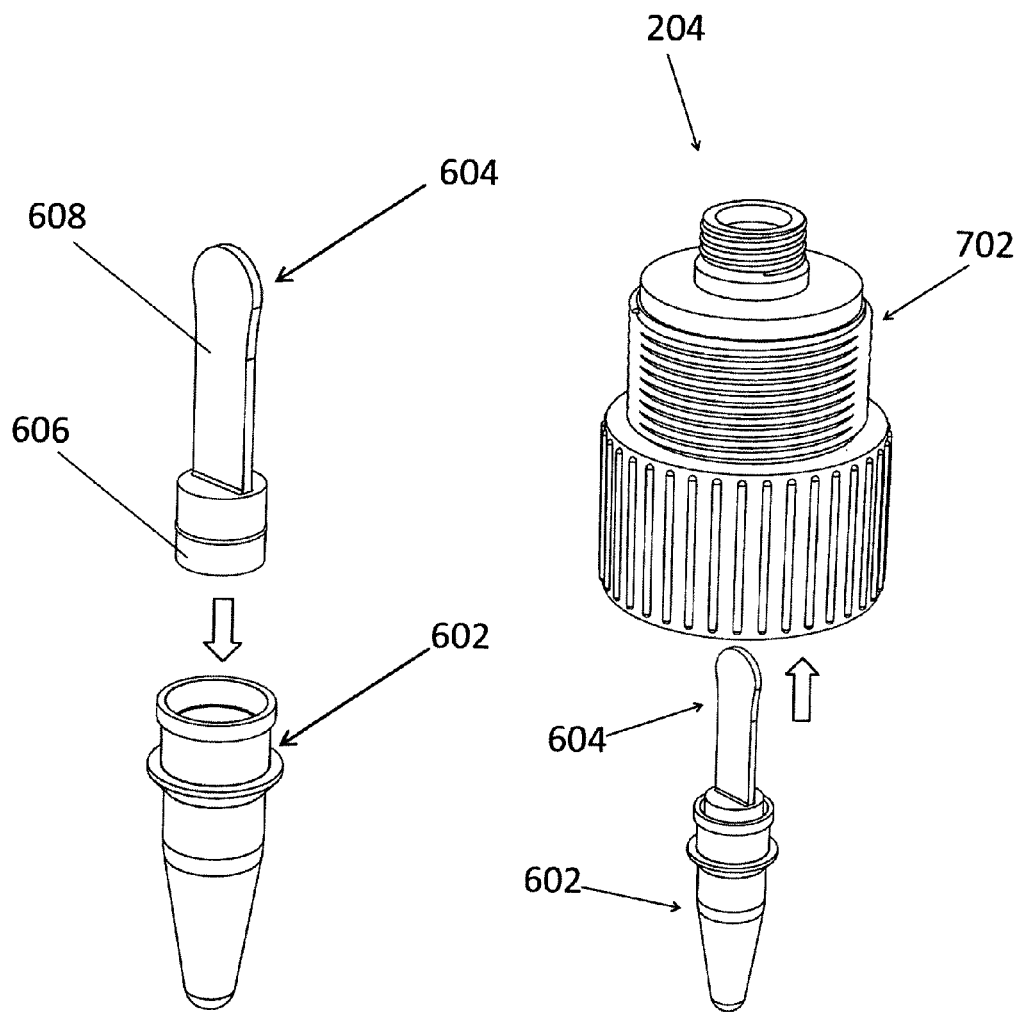
FIGS. 6, 7, 8A and 8B are isometric views illustrating the preparation of a nucleic acid amplification assembly of the kit of FIG. 2.

The assembly or preparation of the nucleic acid amplification assembly begins by dispensing at least one reagent (not shown) into an amplification tube 602, and then sealing the amplification tube 602 with a removable shipping or transport plug or seal 604, as shown in FIG. 6. The reagents may be in wet and/or dry form. In the described embodiment, the amplification tube 602 is a standard PCR tube, but this need not be the case in other embodiments. In any case, like a standard PCR tube, the amplification tube 602 has thin walls and a low thermal mass, allowing it to be rapidly heated while containing fluid samples of about 50-200 ml. The transport plug 604 has a cylindrical base 606 whose curved surface engages with a corresponding dimensioned internal surface of the amplification tube 602 to form a hermetic seal. A handle member 608 extending from the top of the cylindrical base 606 facilitates subsequent removal of the transport plug 604 by a user to allow access to the inner volume of the amplification tube 602 and the reagent(s) stored therein.

Figures 8A, 8B:
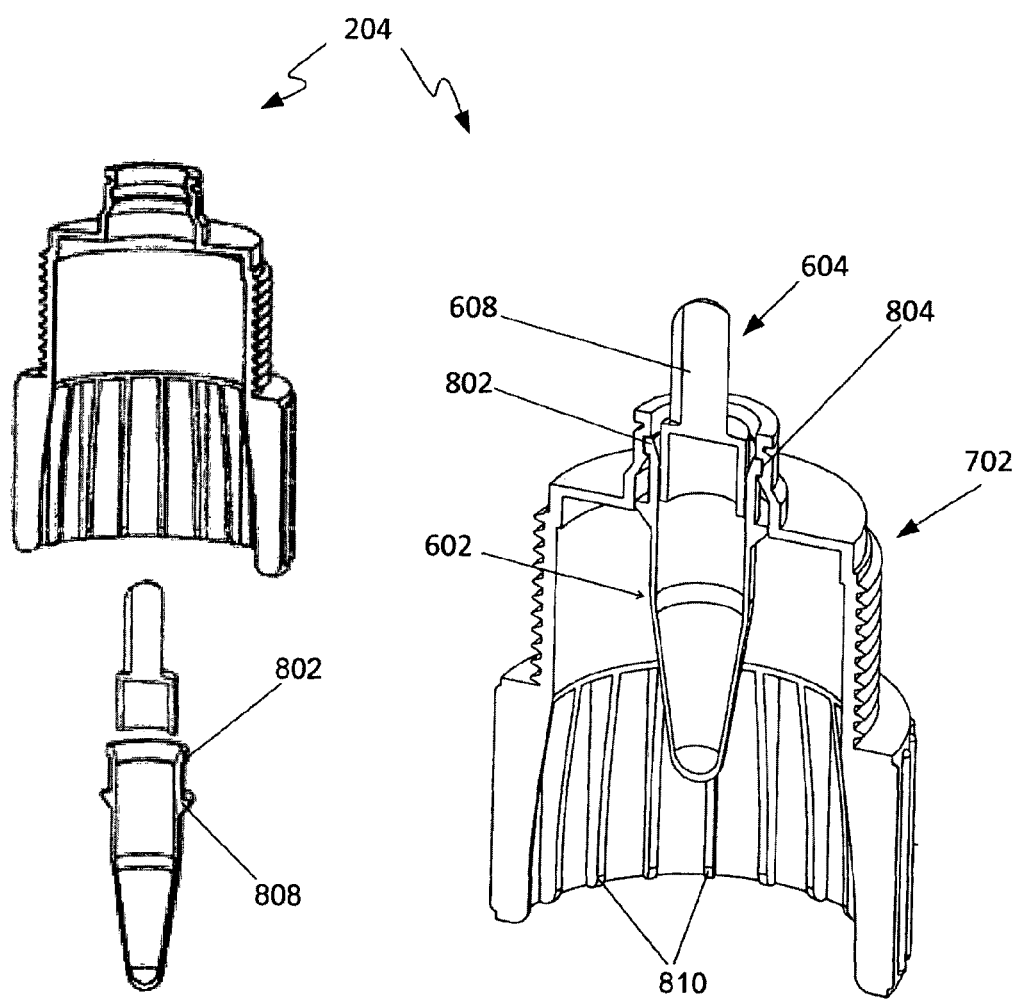
Figure 21:
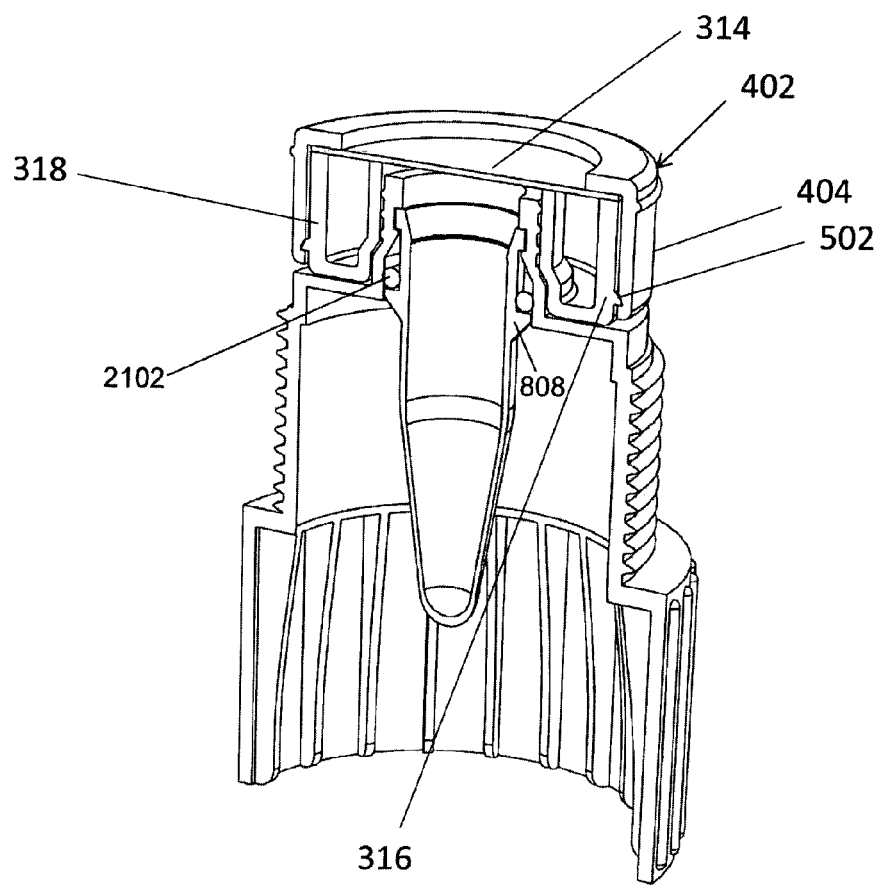
FIG. 21 is a cross-sectional isometric view of the mutually coupled buffer and sample assembly and nucleic acid amplification assembly during nucleic acid amplification.

As shown in FIGS. 7 and 8A, the sealed amplification tube 602 and removable plug 604 are then inserted into the opening of a generally cylindrical support 702. As shown in FIG. 8B, the outer surface portion of the amplification tube 602 engages with and seals against an inner surface of the support 702 by way of a circular projecting rib 802 of the amplification tube 602 and a complementary-shaped circular recess 804 in the inner surface of the support 702. In some embodiments, as shown in FIG. 21, a rubber O-ring seal 2102 forms a seal with a projecting rim or shoulder 808 of the amplification tube 602. In some embodiments, the amplification tube 602 and the support 702 are not separate components but are formed integrally. In any case, the nucleic acid amplification assembly 204 incorporates a low mass amplification tube 602 that can be heated and cooled rapidly like a standard PCR tube, but unlike such tubes can be easily held and manipulated manually by virtue of being mounted to (or formed integrally with) the much larger support 702. Additionally, the handle member 608 of the transport plug 604 is substantially larger and easier to grip than a standard PCR tube cap, thereby facilitating its removal by unskilled users with substantially reduced risk of spillage or mishandling.

Figure 9:
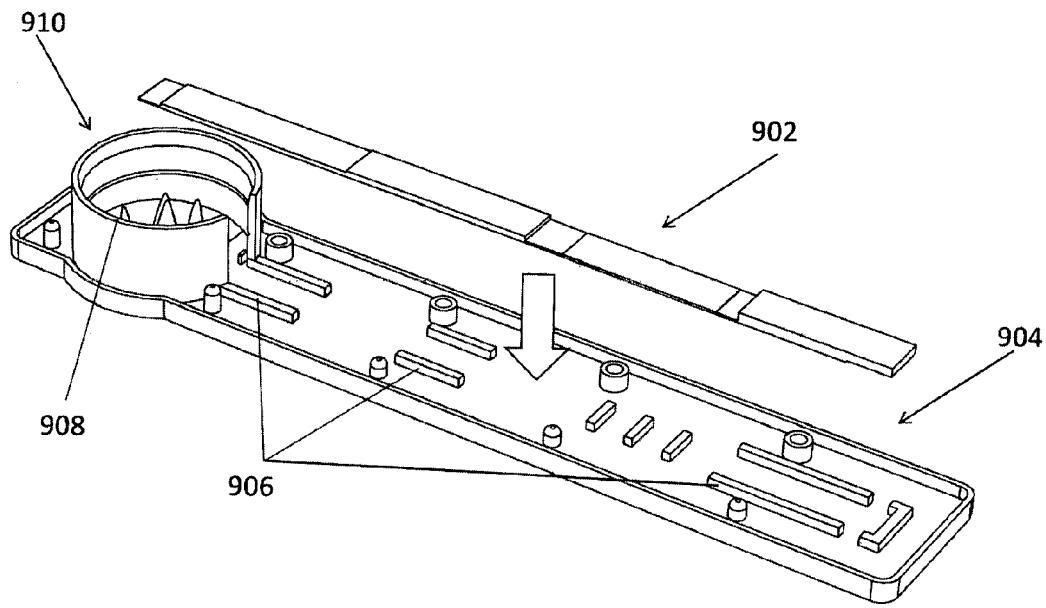
FIGS. 9 to 11 are isometric views illustrating the preparation of a lateral flow test strip assembly of the kit of FIG. 2.
Figure 10:
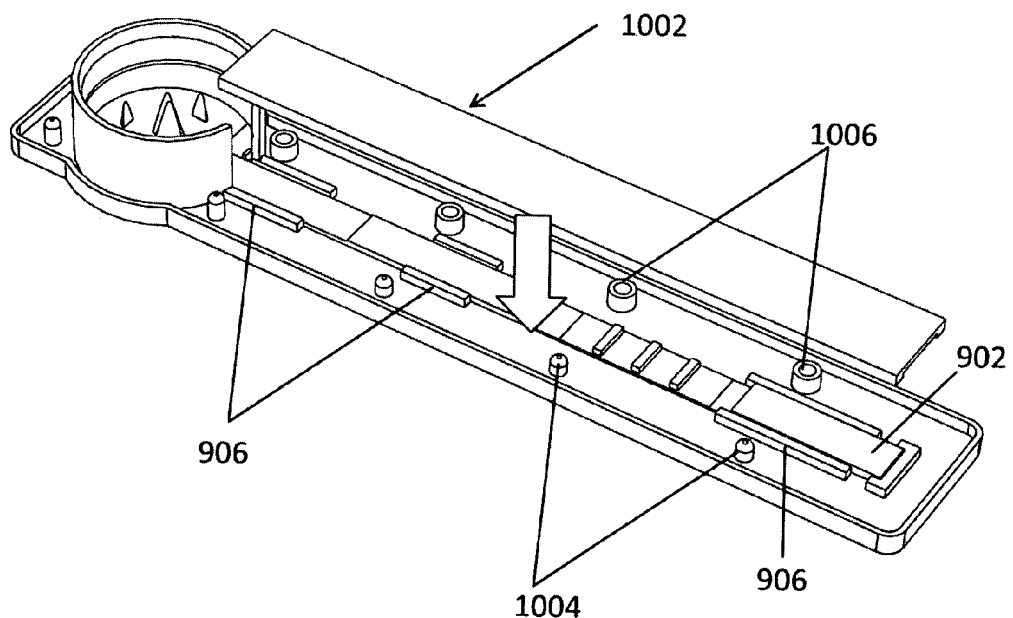
Figure 11:
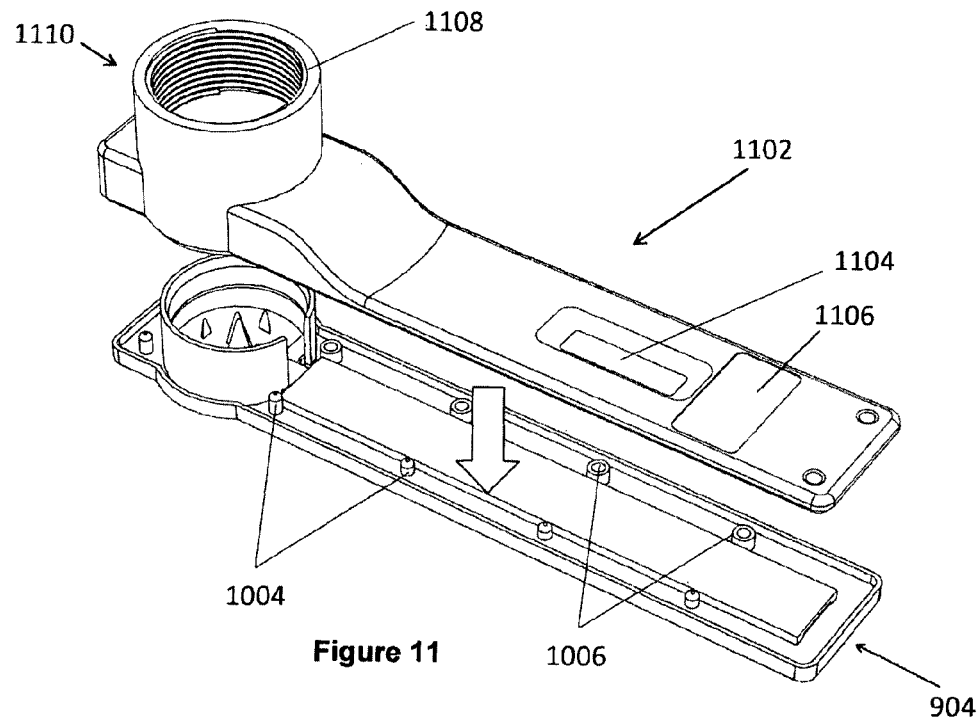

The assembly or preparation of the third component of the kit, the lateral flow test strip assembly 206, is illustrated in FIGS. 9 to 11. As shown in FIG. 9, a prepared test strip 902 is placed into a corresponding receiving region of a supporting base or carriage 904, as represented by the downward arrow. In the described embodiment, the carriage 904 is configured to receive a test strip having the dimensions of the standard test strips used in commercially available lateral flow test strip devices, although it will be apparent that in other embodiments the carriage 904 may be configured to receive test strips with different dimensions. In any case, the test strip 902 is retained within the receiving region by locating ribs 906 projecting upwards from the base and disposed about the periphery of the test strip 902, as shown in FIG. 10.

The carriage 904 also includes a raised collar 908 defining the periphery of a receiving bay 910 for receiving a portion of the nucleic acid amplification assembly, as described further below. As shown in FIG. 10, when mounted in the carriage 904, one end of the test strip 902 extends into the receiving bay 910 through a slot in the raised collar 908 so that the sample application pad 102 of the test strip 902 can absorb fluid in the receiving bay 910, as described further below.

After the test strip 902 is placed in the carriage 904, a transparent cover 1002 is placed over the test strip 902 to protect it while allowing the test strip 902 to be viewed through the transparent cover 1002. The transparent cover 1002 is located in the carriage 904 by two (male and female) sets of locating lugs 1004, 1006, as shown in FIG. 11.

Finally, a top cover 1102 is locked onto the carriage 904 to form a sealable enclosure containing the test strip 902 and transparent cover 1002, thereby forming the complete lateral flow test strip assembly 206. The top cover 1102 includes (male and female) sets of lugs (not visible in the view of FIG. 11) that are complementary to and mate with the male and female sets of locating lugs 1004, 1006 of the carriage 904, thereby engaging the top cover 1102 to the carriage 904. A viewing opening 1104 allows visual access to the test and control lines 114, 116 of the test strip 902 through the top cover 1102 and the transparent cover 1002. A QR code printed on or attached to a QR region 1106 of the top cover 1102 allows the specific test to be reliably and automatically identified.

The top cover 1102 also includes a cylindrical collar 1108 defining a receiving port 1110 for receiving a portion of the nucleic acid amplification assembly 206, as described further below. The internal surface of the collar 1108 is threaded.

Now that the general form and method of assembly of each of the three components or assemblies of the nucleic acid amplification and detection kit have been described, further details of the structure and function of additional features of the assemblies are described below in the context of a typical use of the nucleic acid amplification and detection kit.

Use of the Nucleic Acid Amplification and Detection Test Kit

Figure 34:
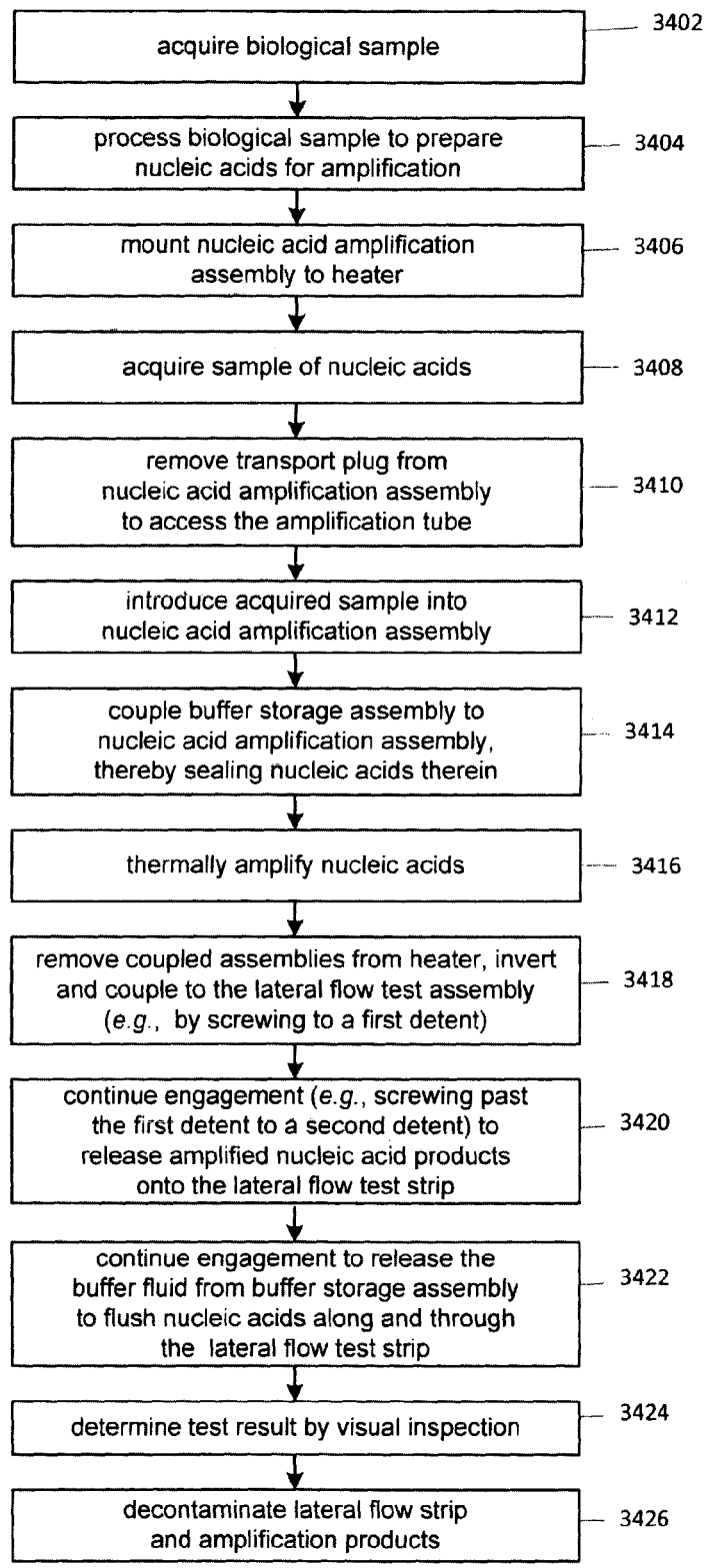
FIG. 34 is a flow diagram of a nucleic acid amplification and detection method in accordance with an embodiment of the present invention.

In order to use the nucleic acid amplification and detection kit, an end-user of the bit performs a nucleic acid amplification and detection method, as shown in FIG. 34.

A typical nucleic acid detection test as described, herein begins at step 3402 with the acquisition of a biological sample. The sample may be, for example, in the form of a small volume of blood or other biological fluid, or a swab taken from a subject. In order to prepare the sample for a subsequent test, it is typically processed at step 3404 to expose nucleic acids in the sample for amplification. However, it should be noted that some tests (e.g., E. coli sampling) may not require a separate sample preparation step, and any required sample preparation chemistry can be included in the amplification tube.

Figure 12:
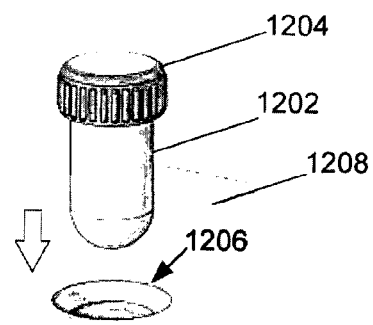
FIGS. 12 to 20 are isometric views illustrating the typical steps required to perform sample preparation and nucleic acid amplification using the buffer storage assembly and the nucleic acid amplification assembly of the kit of FIG. 2.
Figure 13:
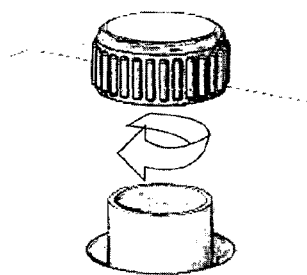
Figure 14:
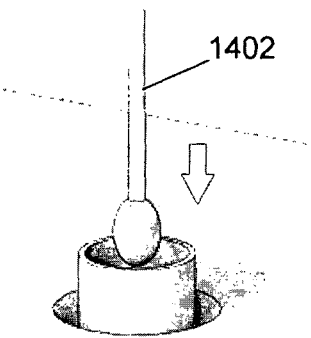
Figure 15:
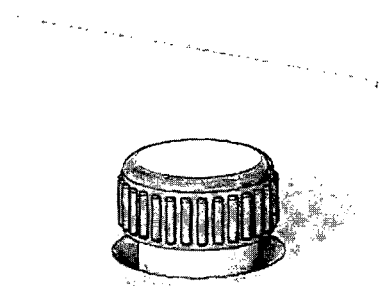

As shown in FIG. 12, a standard sample preparation tube 1202 (with cap 1204) containing a buffer solution and lysis components is placed into a receiving bay 1206 of a heater block or apparatus 1008. As shown in FIGS. 13 to 15, the cap 1204 is removed from the sample preparation tube 1202, the sample (e.g., drop of biological fluid or swab 1402) is added to the contents of the sample preparation tube 1202, and then the cap 1204 is replaced to seal the tube 1202 as shown in FIG. 15. The contents are then heated as required to perform the preparation and lysis of the sample, thereby exposing the nucleic acids for subsequent amplification.

After a nucleic acid sample has been prepared at step 3404, the kit can be used to rapidly and conveniently perform nucleic acid amplification on the sample, and lateral flow testing of the resulting amplification products.

Figure 16:
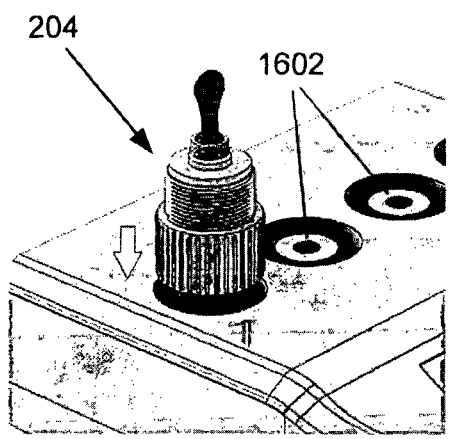

As shown in FIG. 16, the nucleic acid amplification assembly 204 is placed into a receiving port of a heater block workstation or apparatus 1008. The receiving port includes a heating element 1602 in the form of a hollow open-ended cylinder whose dimensions correspond to those of the annular region (as shown in FIGS. 8B and 21) within the nucleic acid amplification assembly 204, so that the heating element 1602 wraps around and comes into intimate contact with the lower portion of the amplification tube 602 mounted therein, thereby ensuring efficient thermal conduction therebetween.

Figure 17:
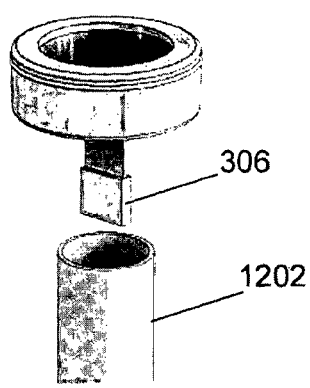

As shown in FIG. 17, at step 3408 the cap 1204 is removed from the sample preparation tube 1202, and the sample collection pad 306 of the buffer storage assembly is inserted into the sample preparation tube 1202 so that a sample of the nucleic acids can be absorbed into the sample collection pad 306. In embodiments where the buffer storage assembly does not include the sample collection pad 306, a sample can be acquired by use of a pipette or dropper, which as described above is included as part of the kit in some embodiments.

Figure 18:
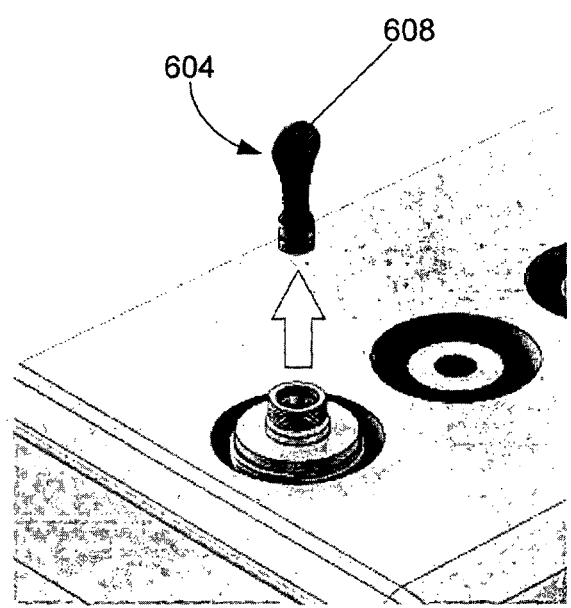
Figure 19:
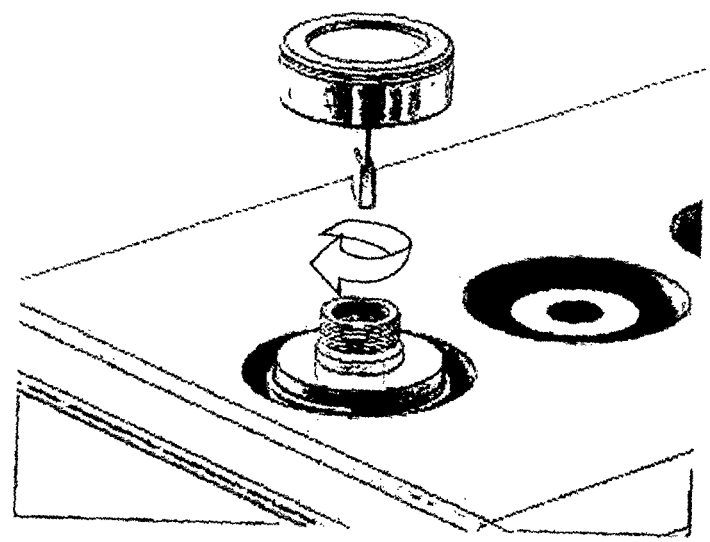
Figure 20:
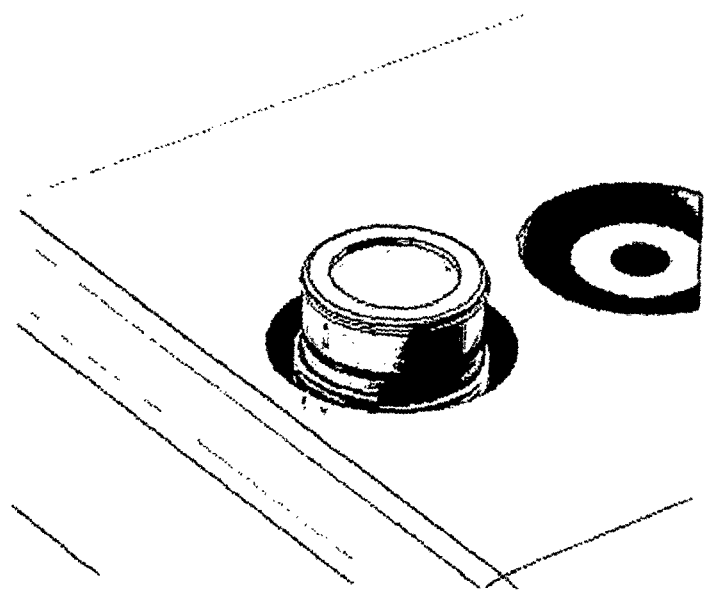

As shown in FIG. 18, the transport plug 604 is removed from the amplification tube 602 by pulling upwards on the handle member 608 at step 3410. Where a pipette or dropper has been used to acquire a sample of the nucleic acids, it is now used to dispense the sample into the open top of the amplification tube 602 at step 3412. In any case, at step 3412, the buffer storage assembly 202 is then coupled to the nucleic acid amplification assembly 204 by inserting the sample collection pad 306 and pad support member or paddle 308 (if present) into the opening of the nucleic acid amplification assembly 204 and screwing the annular cap 402 onto the threaded collar 1108 of the nucleic acid amplification assembly 204, as shown in FIG. 19. Vertically oriented elongate ribs 810 disposed about the inner surface of the nucleic acid amplification assembly 204, as shown in FIG. 8B, engage with correspondingly shaped and oriented elongate recesses (not shown) in the heating element 1602 to prevent rotation of the nucleic acid amplification assembly 204 during this step 3414. When the cap 402 is fully screwed onto the nucleic acid amplification assembly 204, as shown in FIG. 20, a one-way latch locks the annular cap 402 onto the nucleic acid amplification assembly 204 in a manner similar to a ratchet and pawl, thus preventing or at least inhibiting subsequent release of the contents of the amplification tube 602 into the environment. It should be noted that all of these steps 3406 to 3414 can be performed by a single hand of a user.

In this coupled configuration, as shown in FIGS. 20 and 21, the nucleic acid sample in the sample collection pad 306 (if present) mixes with the dry reagent(s) in the amplification tube 602, and the nucleic acids are then amplified at step 3416 under the thermal control of the heater block workstation or apparatus. The amplification step 3416 can be any suitable nucleic amplification process, including standard isothermal or cyclic PCR processes. These DNA amplification methods differ in chemistry and the temperature profile used, but have a common goal of increasing the concentration of a specific DNA target oligonucleotide within the sample.

Figure 22:
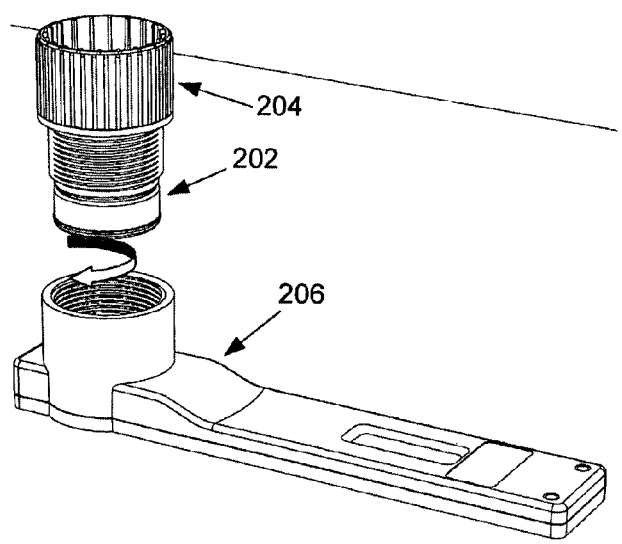
FIG. 22 is an isometric view illustrating the coupling of the already coupled and inverted buffer storage and nucleic acid amplification assemblies to the lateral flow test assembly.
Figure 23:
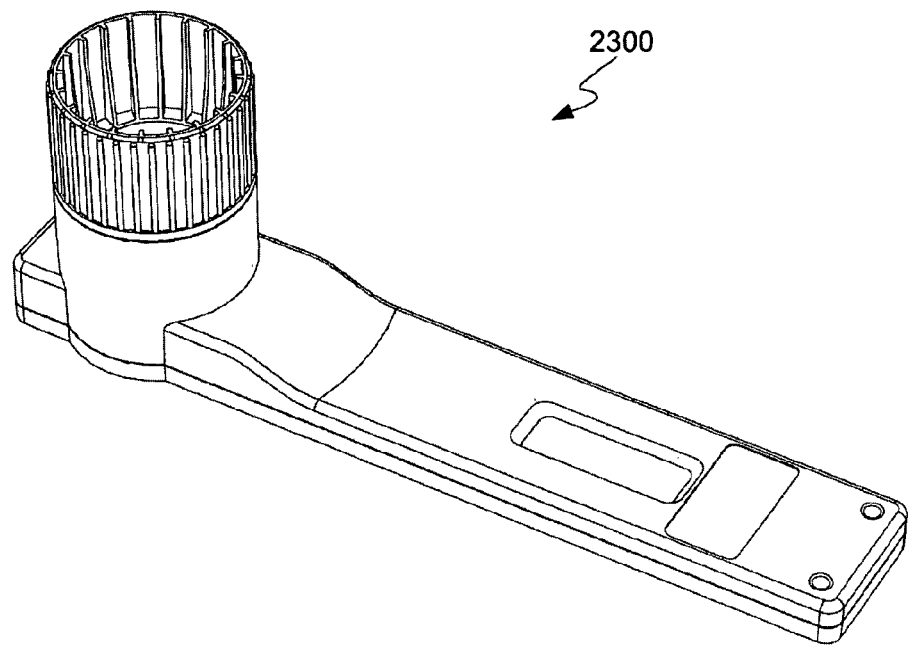
FIG. 23 is an isometric view of the mutually coupled buffer storage, nucleic acid amplification and lateral flow test assemblies.

After the nucleic acids have been amplified, the amplification products are ready to be analysed using the lateral flow test strip assembly 206. At step 3418, the coupled buffer storage assembly 202 and nucleic acid amplification assembly 204 are removed from the heater block workstation or apparatus, inverted, and inserted and screwed into the receiving port 1110 of the lateral flow test strip assembly 206, as shown in FIG. 22, to form the final complete assembly 2300 shown in FIG. 23, where all three (sub-) assemblies are mutually coupled to form a single unit or module.

Figure 24:
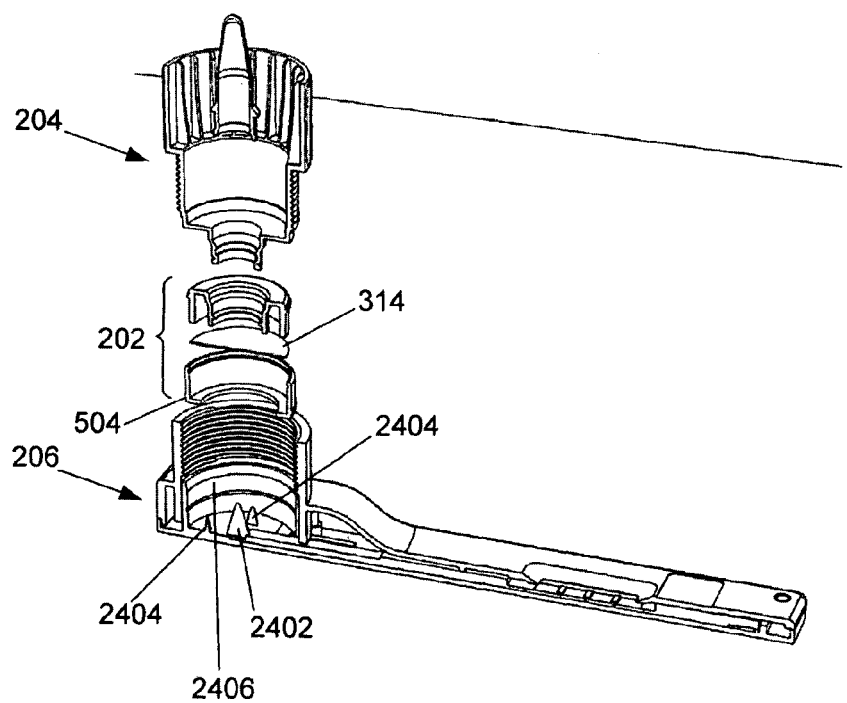
FIG. 24 is an exploded perspective view of the three mutually coupled components of the nucleic acid amplification and detection kit of FIG. 2 during the lateral flow test.
Figure 25:
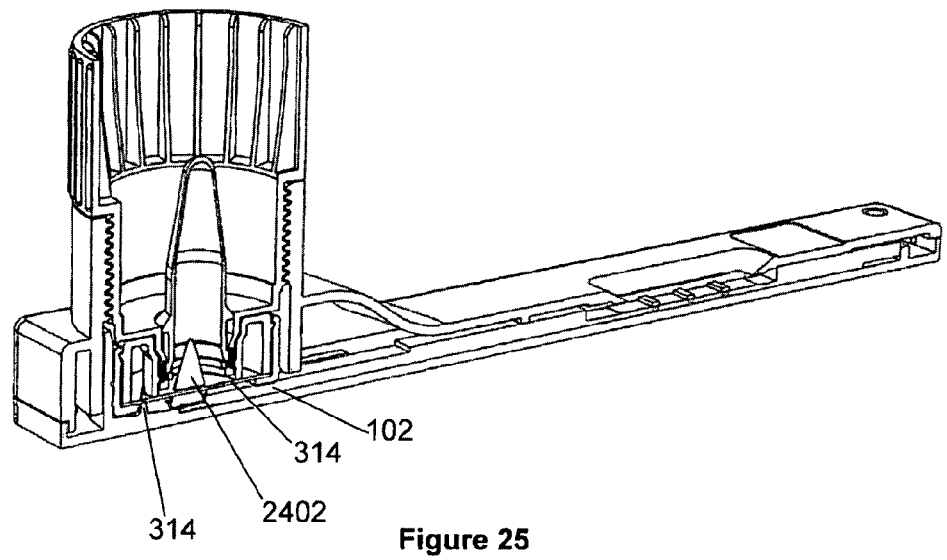
FIGS. 25 and 26 are cross-sectional views of the three mutually coupled assemblies during the lateral flow test.
Figure 26:
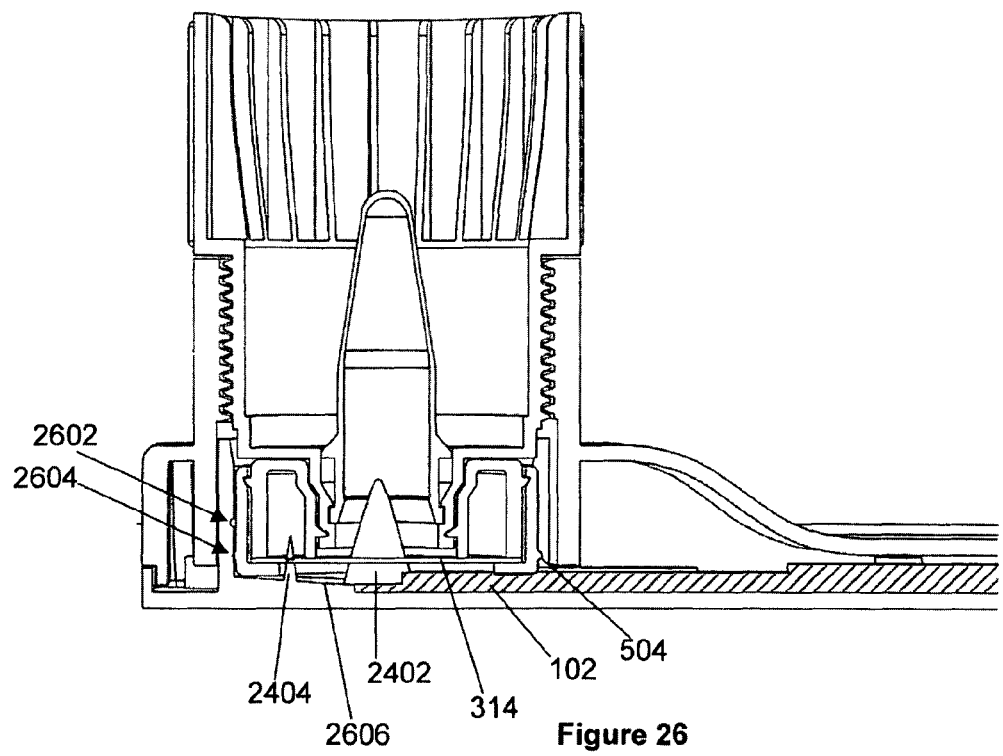

As shown in FIGS. 24 to 26, the carriage 904 of the lateral flow test strip assembly includes a sample release projection 2402 located almost centrally within the circular (in plan view) receiving bay 910, and buffer release projections 2404 disposed about the sample release projection 2402 at locations that substantially correspond to the midpoint of the inner and outer radii of the annular internal cavity or reservoir 312 of the buffer storage assembly 202. As the nucleic acid amplification assembly is screwed into the receiving port 1110 of the lateral flow test strip assembly, a circular rib 504 disposed around the outer cylindrical surface of the cap 402 (as shown in FIG. 5) presses against the inner cylindrical surface 2406 of the lateral flow test strip assembly 206, as shown in FIG. 26 thereby forming a compression seal to prevent the release of any fluids. The inner cylindrical surface 2406 of the lateral flow test strip assembly also includes first 2602 and second 2604 circular recesses for sequentially receiving the circular rib 406 of the cap 402. Continuing the screwing action, the circular rib 406 is received into the first circular recess detent or detents 2602, thus providing a snap or click-type of mutual engagement and (manual and/or aural) feedback to the user, indicating that further screwing of the assemblies together will cause fluid release. In this configuration, the assemblies are securely coupled, but the fluids remain isolated in their respective chambers or reservoirs 312, 602.

Subsequently, as the screwing action is continued further, at step 3420 the sample release projection 2402 is forced through the foil seal 314 into the amplification tube 602 at locations just adjacent the pad support member or paddle 308 (if present), thereby rupturing the frangible seal 314 of the amplification tube 602 and releasing the fluid containing the amplification products from the amplification tube 602, allowing it to flow onto the sample application pad 102 of the test strip 902. The base of the lateral flow assembly has a dish-like shape 2606 to divert the fluid onto the lateral flow strip absorption area 102.

The buffer release projections 2404 are substantially shorter than the sample release projection 2402. Consequently, further rotation of the nucleic acid amplification assembly 204 is required at step 3422 in order to force the buffer release projections 2404 through the frangible foil seal 314 and into the annular internal cavity or reservoir 312 to release the buffer fluid stored therein onto the sample application pad 102 of the test strip 902. The delayed timing of the buffer release has the effect of flushing the released sample fluid along and through the test strip 902. With further screwing action, the circular rib 406 is eventually received into the second circular recess 2604, thus providing feedback to the user that the assemblies are fully engaged and that the buffer solution has been released. Additionally, another asymmetric locking projection or tooth (not shown) engages with a corresponding detent near the end of the screw thread to lock the assemblies together as described above for the cap 402 and nucleic acid amplification assembly, thereby preventing or at least inhibiting subsequent release of the amplification products into the environment. In addition, in some embodiments, the screw thread itself may be sufficiently long and otherwise configured to provide effective sealing of the contents of the assemblies, preventing them from being released into the environment.

Figure 27:
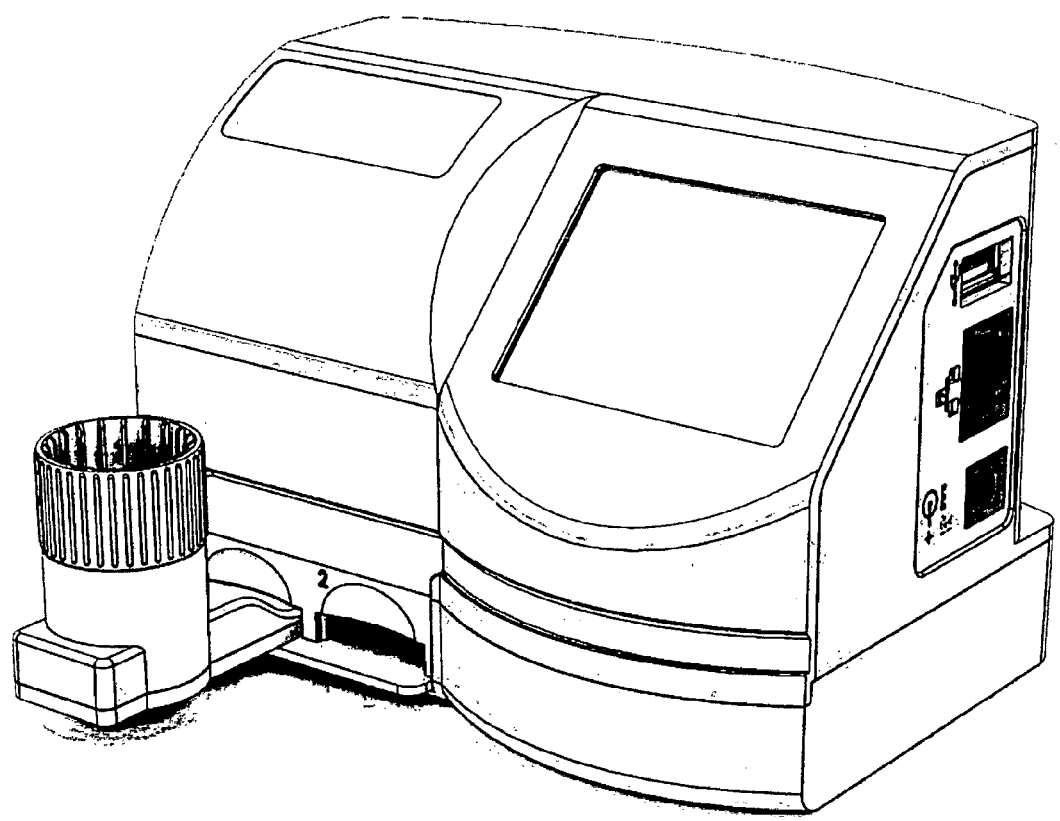
FIG. 27 is illustrates the use of a detection instrument with the nucleic acid amplification and detection kit of FIG. 2 to automatically detect a test result.

If the test and control lines 114, 116 of the test strip 902 cannot be read directly by the eye of the user, or for increased sensitivity or test result traceability and recording, the coupled assemblies can be inserted into a dedicated test reader apparatus at step 3426, as shown in FIG. 27. The test strip 902 provides a visible detection of the target amplified DNA (if present), together with a control output to validate the test.

In an alternative embodiment, as shown in FIGS. 28 to 33, the carriage 904 of the lateral flow test strip assembly includes a larger sample release projection 2802 configured to positively displace substantially all of (or in other embodiments, at least a substantial portion of) the fluid from the inverted amplification tube 602. In testing, it has been found that this general configuration can be advantageous in circumstances where the viscosity and/or surface tension of the fluid within the amplification tube 602 inhibits it from flowing or reliably flowing from the inverted amplification tube 602 onto the sample application pad 102 of the test strip 902 under the influence of gravity alone. In such cases, forcing the larger sample release projection 2802 into the internal volume of the inverted amplification tube 602 positively forces the fluid out of the tube 602.

Figure 31:
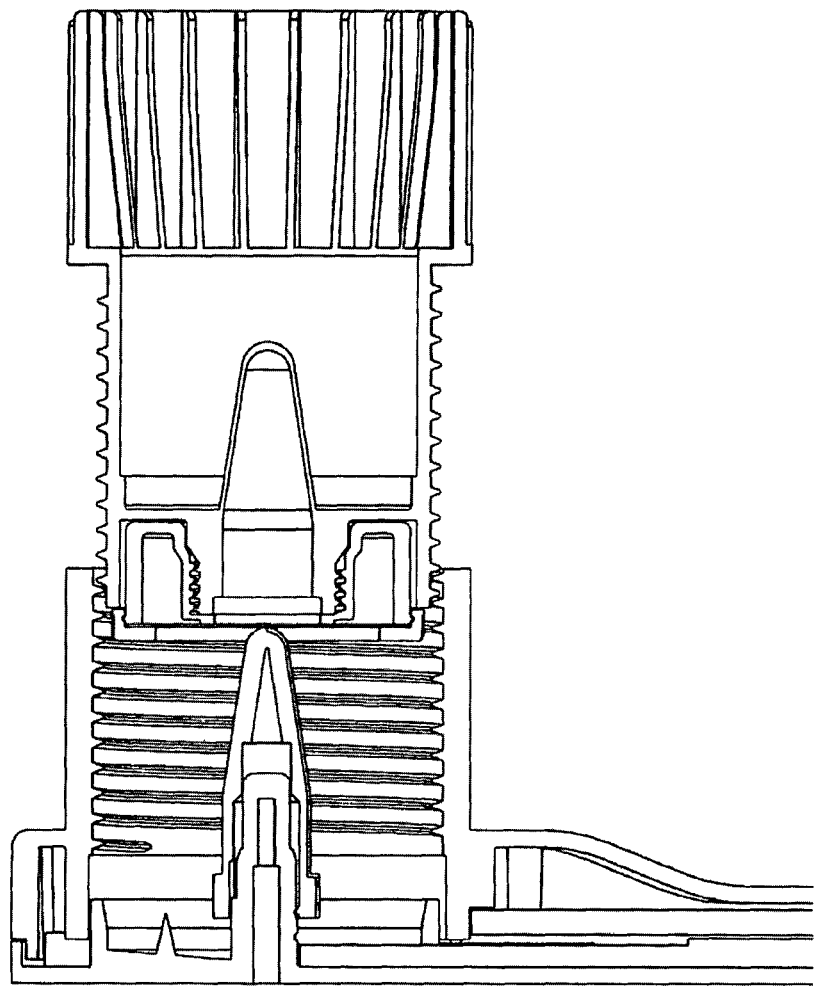
Figure 32:
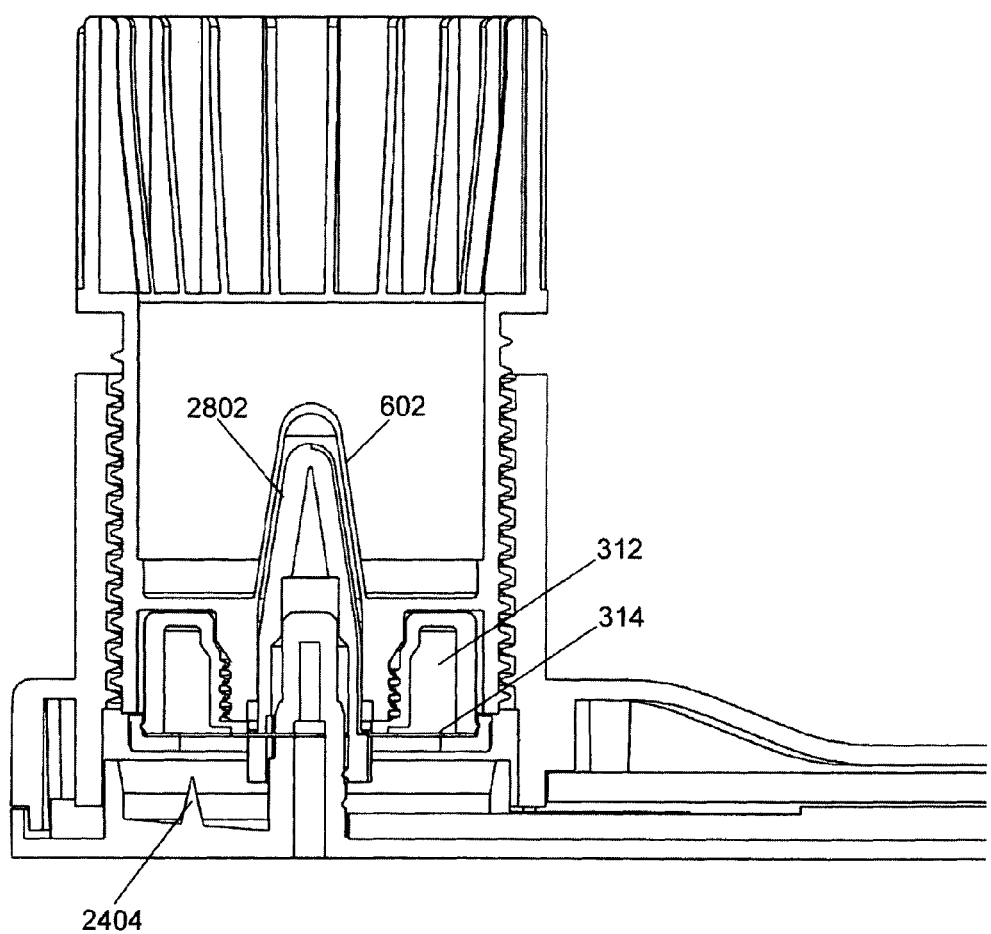
Figure 33:
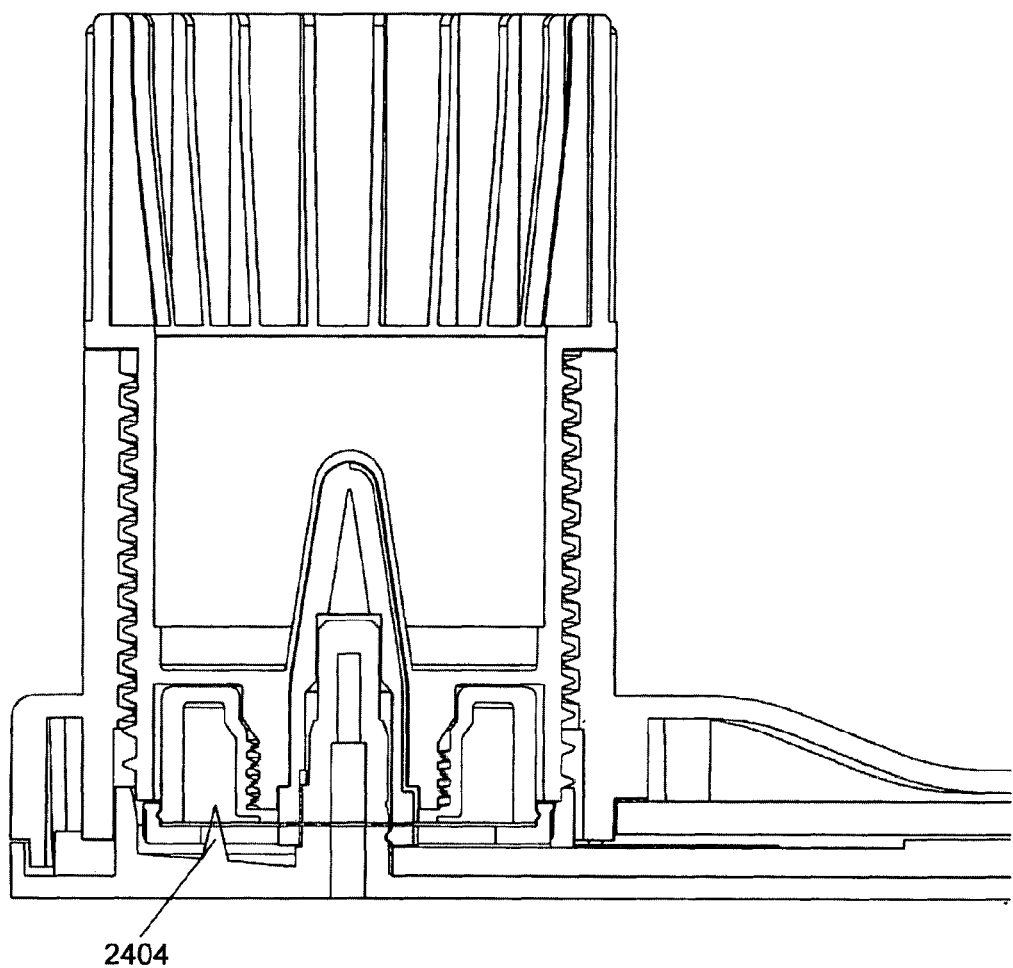

To illustrate this, FIGS. 31 to 33 are cross-sectional side views illustrating successive stages of the penetration of the sample release projection 2802 into the inverted amplification tube 602 as the nucleic acid amplification assembly is screwed into the receiving port 1110 of the lateral flow test strip assembly.

As the nucleic acid amplification assembly is initially located in the receiving port 1110 of the lateral flow test strip assembly and the respective screw threads of those components are initially engaged with one another, the tip of the sample release projection 2802 approaches and eventually contacts the foil seal 314 of the buffer storage assembly, as shown in FIG. 31.

Figure 28:
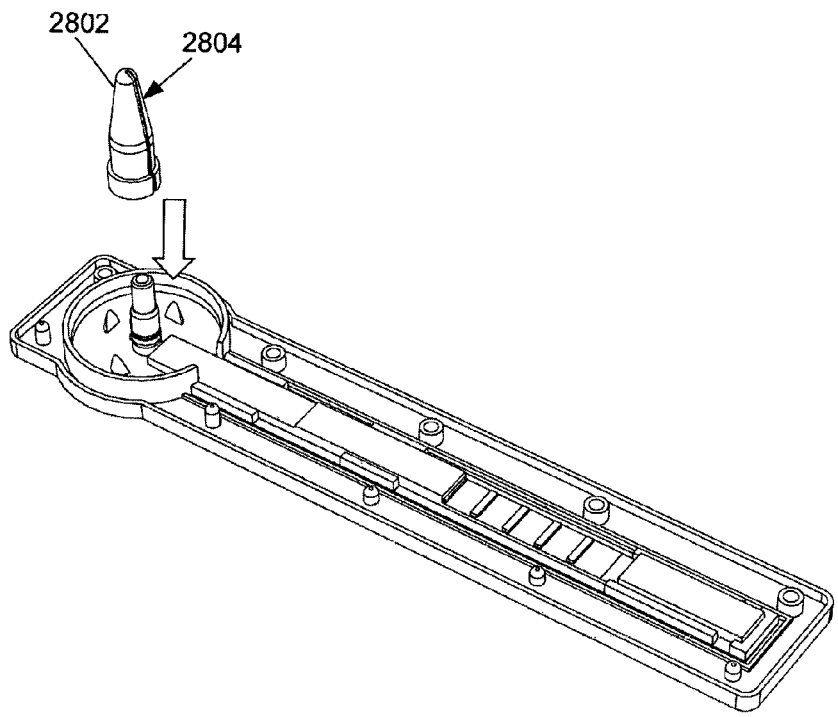
FIGS. 28 and 29 are isometric and exploded cross-sectional views, respectively, of a nucleic acid amplification and detection kit in accordance with an alternative embodiment of the present invention.
Figure 29:
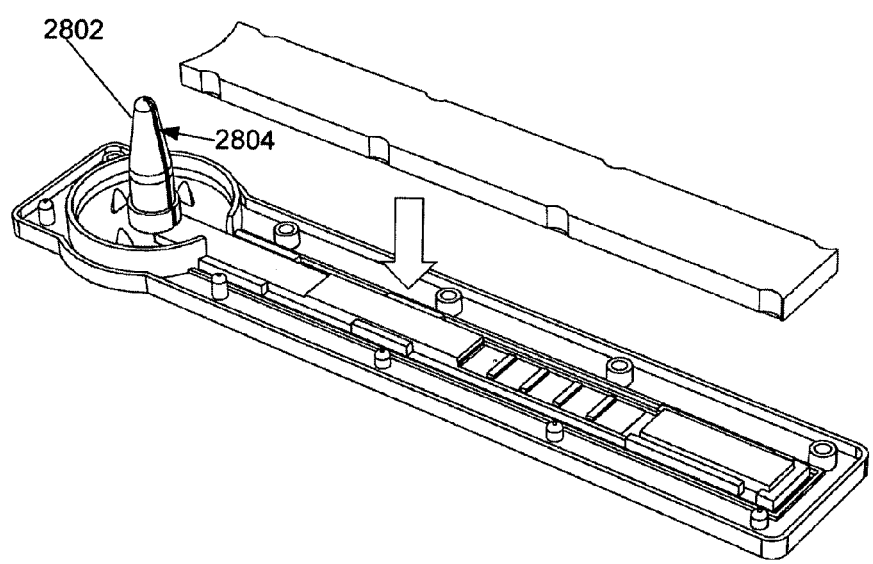
Figure 30:
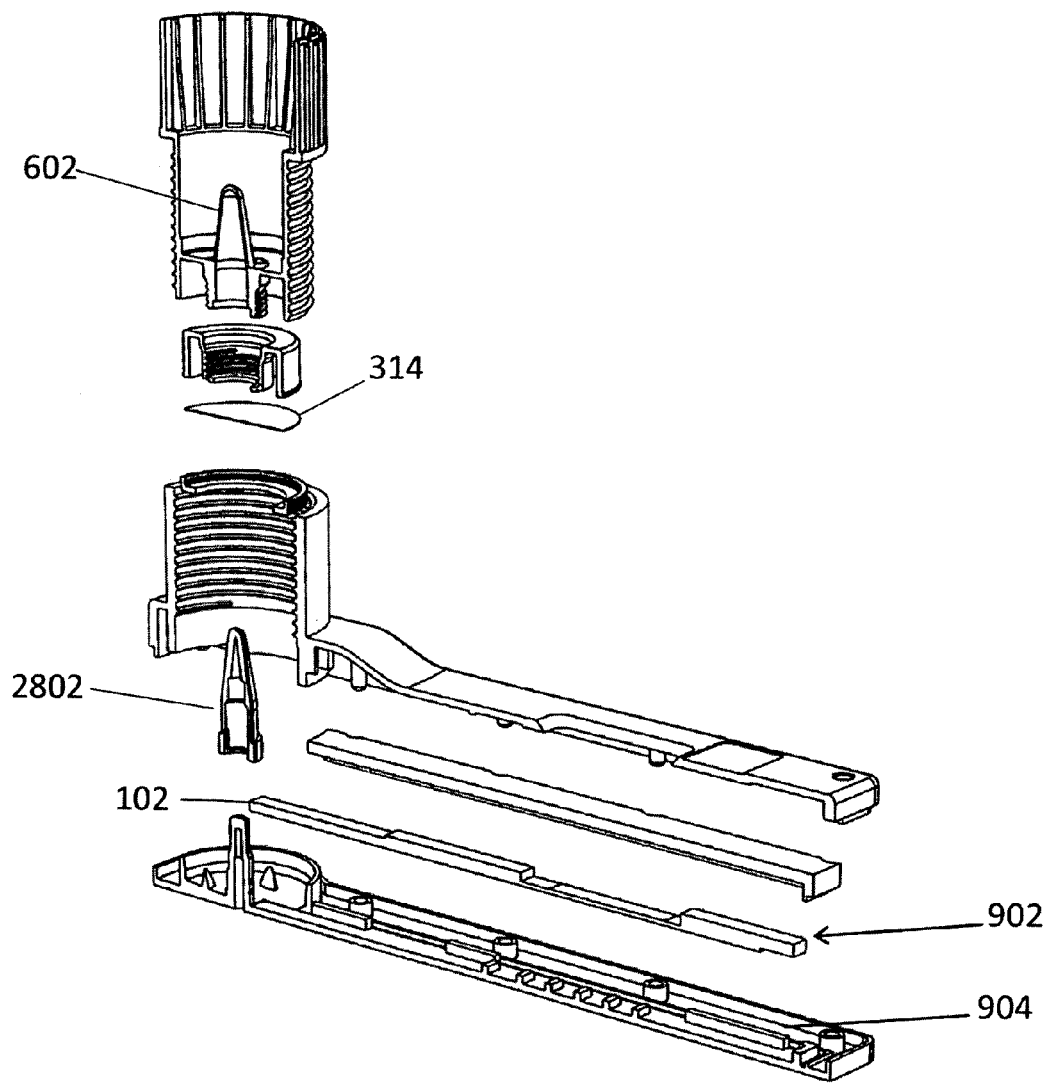
FIGS. 30 to 33 are cross-sectional side views of the nucleic acid amplification and detection kit of FIGS. 28 and 29, illustrating successive stages of the penetration of the sample release projection into the amplification tube as the nucleic acid amplification assembly is screwed into the receiving port of the lateral flow test strip assembly.

As the assemblies are further screwed together, the sample release projection 2802 ruptures the foil seal 314 and begins occupying the internal volume of the inverted amplification tube 602, as shown in FIG. 32, thereby positively displacing the amplification products fluid, and forcing it out of the inverted amplification tube 602. The sample release projection 2802 includes at least one opening or channel 2804, as shown in FIGS. 28 and 29, to allow the liquid to flow out through or past the sample release projection 2802 as the latter fills the inverted amplification tube 602. In the position shown in FIG. 32, which is close to the final end position of maximum mutual engagement, the annular internal cavity or reservoir 312 remains sealed.

At the final position shown in FIG. 33, all of the amplification products fluid has been displaced and has flowed out onto the absorption pad 102 of the lateral flow strip 902. As with the embodiments described above, at this position, the screw thread includes a locking projection (not shown) that engages with a detent in the carriage 904 of the lateral flow test strip assembly to retain the assemblies in this final position and prevent the nucleic acid amplification assembly 204 from being unscrewed from the lateral flow test strip assembly 206.

Additionally, as shown in FIG. 33, in this position the buffer release projections 2404 have been forced through and around the foil seal 314 and into the annular internal cavity or reservoir 312 at step 3422 to release the buffer fluid stored therein onto the sample application pad 102 of the test strip 902. As with the embodiment described above, the delayed timing of the buffer release has the effect of flushing the limited volume of amplified products along and through the test strip 902.

Mixing

In some circumstances, mixing of the amplification tube contents may be required or desired, particularly where the amplification reagents are dried or lyophilised and need to be reconstituted into a liquid sample. In order to address this need, the amplification step 3416 can use a heater block mounted to a source of mechanical vibration so that the heater block (and consequently the contents of the amplification tube 602 when mounted therein, as shown in FIG. 20) can be vibrated at one or more frequencies to cause mixing of the amplification tube contents. In one arrangement, this is achieved by mounting the heating block to an ultrasonic transducer excited by a high frequency AC signal. Particles or beads may be added to the reagent mix to enhance the action of vibration mixing.

An alternative mixing arrangement is to add one or more paramagnetic beads to the reagent mix, where the beads can be moved in the solution by an externally applied magnetic field to induce mixing. The external magnetic field can be as simple as a fixed magnet in the top region of the heater block so that the bead is lifted up from the bottom of the amplification tube 602 through the solution as the amplification tube 602 is inserted into the heater block. The user instructions can specify that the amplification tube 602 should be inserted into and removed from the heater block a (specified) number of times (e.g., 2-3) prior to leaving it in the heater block to perform the nucleic acid amplification therein. In one arrangement, the electronics that control the heater block include a switch or sensor that detects the presence of the tube 602 within the heater block and can be configured to prompt the user by a visual display and/or transducer audio to correctly complete the mixing and finally remove the amplified products at the completion of the amplification stage.

In an alternative arrangement, the tube remains fixed in the heater block and the magnetic mixing is driven by the movement of one or more beads under the influence of a changing magnetic field. In this arrangement, the beads are moved or oscillated or are drawn to the top of the solution and allowed to fall under the influence of gravity. In another arrangement, a moving permanent magnet in proximity to the tube is used to induce movement of one or more paramagnetic beads and thus cause mixing. This arrangement can include a solenoid or motor driven mechanism or a manually operated button or lever mechanically coupled to the magnet.

Decontamination and Backflow

The risk of contamination of the working environment by either the pathogen under test or amplified DNA products is a significant issue for the effective and safe operation of diagnostic tests. The described embodiments of the invention include nucleic acid amplification and detection kits configured to sequester the amplified DNA products and to prevent their accidental release into the environment.

In some embodiments, the risk of contamination is further reduced by incorporating one or more decontamination components in the lateral flow strip assembly 206. These decontamination components provide subsequent decontamination and disinfection of the lateral flow strip and the amplified sample products at step 3426 once the results of the test are available to the user at step 3424. The decontamination features and methods described below thus provide a further safety enhancement over mechanically sealing the amplification products within the coupled assemblies 202, 204, 206.

In some embodiments, a decontamination chemistry such as a slow reacting oxidation agent is incorporated into the sample buffer solution so that the test is performed normally and the test result displayed prior to the decontamination chemistry breaking down and decontaminating the amplification and sample products.

In another embodiment, the properties of the waste absorbing pad 108 at the end of the lateral flow strip are exploited to achieve the time delay. The waste pad 108 of a lateral flow strip drives the continued capillary action of the strip as it absorbs fluid flowing through the strip, thereby allowing more reagents to progress through the test membrane 106. As typically occurs with standard lateral flow tests, after a period time the source of fluid flowing along the strip becomes exhausted, and as the strip starts to dry out, the larger volume of absorbed fluid retained within the relatively large waste pad 108 is available to allow backflow of the sample and buffer fluid from the waste pad 108 back along the test strip in the opposite direction. Backflow is normally a problem with standard lateral flow tests, as it requires the test result be read relatively quickly before the backflow obscures or destroys the test result. In some embodiments of the present invention, this backflow property of lateral flow strips is exploited to drive a decontamination stage.

In some embodiments, a decontamination reagent such as an oxidising agent or a nuclease enzyme is previously dried in the waste pad 108 as part of the strip manufacturing process. As the sample buffer or wash solution is absorbed into the waste pad 108, this reagent is reconstituted into solution. As the fluid along the strip begins to dry out, a proportion of the absorbed buffer solution now containing decontamination regents flows back through the strip by backflow, thereby providing effective chemical decontamination of the whole strip, including the membrane 106 and all three pads 102, 104, 108.

An additional or alternative decontamination arrangement is to provide a UV decontamination in the reader instrument configured to receive most or all of the consumable within a cover or hood, to read and display the results of the test, and then to turn on a UV illumination source such as UV light emitting diodes to provide UV decontamination to all of the wetted areas within the device.

The nucleic acid amplification and detection kits described herein provide a convenient, low cost platform for determining the presence of specific DNA within a sample, and have particular application to agricultural, food, environmental, veterinary, biomedical or medical test applications. The kits can be used with isothermal or cycled (e.g., PCR) amplification methods to increase the presence of a particular DNA target in a sample, provide a convenient and simplified means of fluid management, and use a simple (and, in some embodiments, standard) lateral flow test strip for conducting the detection stage of a molecular DNA diagnostic test.

Standard PCR tubes are optimised for nucleic amplification and containment, but are not generally suited for dispensing operations, and consequently pipettes are normally used to sample amplification products for testing. By incorporating such an amplification tube (whether an actual standard PCR tube or an equivalent thereto) into the nucleic acid amplification assemblies described herein, the advantageous properties of standard PCR tubes are exploited for amplification. By subsequently inverting the nucleic acid amplification assemblies and hence the amplification tubes disposed therein for dispensing, the assemblies and methods described herein allow the amplification products to be conveniently dispensed from the amplification tubes without the need for additional handling and/or the inconvenient use of pipettes and the like. This avoids direct handling of the amplification tubes, and allows the testing to be conveniently and reliably performed by inexpert users, without fear of contaminating the testing environment, whether in a laboratory setting or at the point of collection, including in the field, or at the Point of Care while the patient is waiting for the test result. In recent years, many doctor offices and many pharmacies have performed diagnostic tests for the detection of infectious agents, including Influenza A and B, RSV, or *Streptococcus* A. The assemblies herein described bring the high level of performance of molecular amplification technology to the Point of Collection or Point of Care, resolving the sensitivity problems inherent to the current immunoassay-based tests used in these settings.

The described assemblies and kits enable nucleic acid amplification and testing to be performed by inexpert users on samples contained within a disposable cartridge or assembly. These and other features described herein allow reduced complexity and provide a compact, portable, and relatively low cost kit.

Many modifications will be apparent to those skilled in the art without departing from the scope of the present invention.

The invention claimed is:

1. A nucleic acid amplification and detection kit, including:
 a buffer storage assembly, including a buffer storage reservoir storing a buffer solution therein;
 a nucleic acid amplification assembly including a nucleic acid amplification reservoir storing one or more reagents therein and configured to receive a sample containing nucleic acid for amplification therein,
 wherein the buffer storage assembly is configured to couple with the nucleic acid amplification assembly to seal within the nucleic acid amplification reservoir the sample containing nucleic acid and amplification products of said amplification; and
 a test strip assembly including a lateral flow test strip disposed therein, the test strip assembly and the coupled nucleic acid amplification and buffer storage assemblies being configured to couple with one another and including one or more solution release components to release the amplification products from the nucleic acid amplification reservoir onto the lateral flow test strip for testing, and to release the stored buffer solution from the buffer storage reservoir to flush the released amplification products along the lateral flow test strip.

2. The nucleic acid amplification and detection kit of claim 1, wherein the solution release components are configured to release the amplification products onto the lateral flow test strip prior to releasing the buffer solution onto the lateral flow test strip.

3. The nucleic acid amplification and detection kit of claim 1, wherein the buffer storage reservoir includes a rupturable membrane that seals the buffer solution within the buffer storage reservoir, and the solution release components includes at least one buffer release component that ruptures the membrane to allow said release of the buffer solution from the buffer storage reservoir.

4. The nucleic acid amplification and detection kit of claim 3, wherein a first portion of the rupturable membrane seals the buffer solution within the buffer storage reservoir, and a second portion of the rupturable membrane seals the amplification products within the nucleic acid amplification reservoir, and the solution release means includes at least one amplification products release component that ruptures the second portion of the membrane to allow release of the amplification products from the nucleic acid amplification reservoir.

5. The nucleic acid amplification and detection kit of claim 4, wherein the amplification products release component includes a projection that projects into the nucleic acid amplification reservoir to displace the amplification products therefrom.

6. The nucleic acid amplification and detection kit of claim 1, wherein the solution release components are configured to automatically release the amplification products and the stored buffer solution during coupling of the test strip assembly to the coupled nucleic acid amplification and buffer storage assemblies.

7. The nucleic acid amplification and detection kit of claim 1, wherein the test strip assembly is coupled to the coupled nucleic acid amplification and buffer storage assemblies by a screwing action.

8. The nucleic acid amplification and detection kit of claim 1, including a test strip assembly locking component to prevent or at least inhibit decoupling of the test strip assembly from the coupled nucleic acid amplification and buffer storage assemblies.

9. The nucleic acid amplification and detection kit of claim 1, including a nucleic acid amplification assembly locking component to prevent or at least inhibit decoupling of the coupled nucleic acid amplification and buffer storage assemblies.

10. The nucleic acid amplification and detection kit of claim 1, wherein the buffer storage assembly includes a cap or lid incorporating the buffer storage reservoir, and the buffer storage reservoir is in the form of an annular cavity within the cap or lid, the cavity being sealed by a rupturable membrane disposed on the outer surface of the cap or lid when the cap or lid seals the nucleic acid amplification reservoir.

11. The nucleic acid amplification and detection kit of claim 1, wherein the nucleic acid amplification assembly includes a generally cylindrical support to support the nucleic acid amplification reservoir, the support being configured to couple with the buffer storage assembly and with the test strip assembly, the nucleic acid amplification reservoir being in the form of a PCR tube having a removable sealing component.

12. The nucleic acid amplification and detection kit of claim 11, wherein the removable sealing component is in the form of a plug having a handle to facilitate removal of the plug from the nucleic acid amplification reservoir by a user.

13. The nucleic acid amplification and detection kit of claim 11, wherein the support is configured to couple with the buffer storage assembly in an upright orientation so that the amplification products are retained at the base of the PCR tube by gravity, and to couple with the test strip assembly in an inverted orientation so that gravity acts to draw the amplification products away from the base of the PCR tube.

14. The nucleic acid amplification and detection kit of claim 1, wherein the nucleic acid amplification reservoir stores one or more magnetic beads in addition to the one or more reagents.

15. The nucleic acid amplification and detection kit of claim 1, including one or more decontamination components configured to automatically destroy the amplification products subsequent to said testing.

16. The nucleic acid amplification and detection kit of claim 15, wherein the decontamination components include a slow acting decontamination agent included in the buffer solution.

17. The nucleic acid amplification and detection kit of claim 15, wherein the decontamination components include a decontamination agent stored in a waste pad of the lateral flow test strip, whereby backflow from the waste pad decontaminates the lateral flow test strip.

18. The nucleic acid amplification and detection kit of claim 1, wherein the buffer storage assembly includes a sample capture component for capturing a sample containing nucleic acid, the sample capture component being arranged so that the act of coupling the buffer storage assembly to the nucleic acid amplification assembly requires the sample capture component to be introduced into the nucleic acid amplification reservoir, thereby also introducing the captured sample containing nucleic acid into the nucleic acid amplification reservoir for amplification therein.

19. The nucleic acid amplification and detection kit of claim 18, wherein the buffer storage assembly includes a cap or lid incorporating the buffer storage reservoir, and the sample capture component includes an absorbent pad disposed at one end of an elongate member, the other end of the elongate member being attached to the cap or lid.

20. The nucleic acid amplification and detection kit of claim 19, wherein the buffer storage assembly is configured to couple with the nucleic acid amplification assembly by introducing the absorbent pad and elongate member into the nucleic acid amplification reservoir and then sealing the nucleic acid amplification reservoir with the cap or lid.

21. A nucleic acid amplification and detection method, including:
  introducing a sample containing nucleic acid into a nucleic acid amplification reservoir of a nucleic acid amplification assembly;
  coupling to the nucleic acid amplification assembly a buffer storage assembly to seal the sample containing nucleic acid within the nucleic acid amplification reservoir, the buffer storage assembly including a buffer storage reservoir storing a buffer solution therein;
  performing nucleic acid amplification to generate amplification products within the sealed nucleic acid amplification reservoir;
  inverting the coupled buffer storage and nucleic acid amplification assemblies to facilitate removal of the amplification products therefrom;
  coupling the coupled buffer storage and nucleic acid amplification assemblies to a test strip assembly including a lateral flow test strip disposed therein;
  releasing the amplification products from the nucleic acid amplification reservoir onto the lateral flow test strip; and
  releasing the buffer solution from the buffer storage reservoir onto the lateral flow test strip to flush the amplification products along the lateral flow test strip;
  wherein the amplification products remain sealed within the coupled assemblies.

22. The method of claim 21, including coupling the coupled assemblies to a test strip reader instrument to determine a test result, and exposing the coupled assemblies to a UV light source to decontaminate the coupled assemblies.

* * * * *